(12) United States Patent
Alisi et al.

(10) Patent No.: US 8,507,528 B2
(45) Date of Patent: Aug. 13, 2013

(54) 2-ALKYL-INDAZOLE COMPOUNDS FOR THE TREATMENT OF CERTAIN CNS-RELATED DISORDERS

(75) Inventors: Maria Alessandra Alisi, Rome (IT); Nicola Cazzolla, Albano Laziale (IT); Guido Furlotti, Rome (IT); Caterina Maugeri, Rome (IT); Rosella Ombrato, San Lorenzo Del Vallo (IT); Lorenzo Polenzani, Grottaferrata (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 272 days.

(21) Appl. No.: 12/516,091

(22) PCT Filed: Nov. 19, 2007

(86) PCT No.: PCT/EP2007/010000
§ 371 (c)(1),
(2), (4) Date: Jul. 14, 2009

(87) PCT Pub. No.: WO2008/061688
PCT Pub. Date: May 29, 2008

(65) Prior Publication Data
US 2010/0056573 A1  Mar. 4, 2010

(30) Foreign Application Priority Data
Nov. 22, 2006  (IT) ................ M106A002230

(51) Int. Cl.
*A61K 31/445* (2006.01)
*C07D 211/32* (2006.01)
*C07D 231/56* (2006.01)

(52) U.S. Cl.
USPC ............... 514/322; 546/199; 548/362.5

(58) Field of Classification Search
None
See application file for complete search history.

(56) References Cited

U.S. PATENT DOCUMENTS

| | | | | |
|---|---|---|---|---|
| 4,436,913 | A * | 3/1984 | Molnar et al. | 548/311.7 |
| 5,631,270 | A * | 5/1997 | Effland et al. | 514/337 |
| 5,705,453 | A | 1/1998 | Kyomura et al. | |
| 5,945,434 | A * | 8/1999 | Suzuki et al. | 514/322 |
| 2004/0110815 | A1 | 6/2004 | Cournoyer et al. | |
| 2006/0030612 | A1* | 2/2006 | Steffan et al. | 514/406 |
| 2006/0106084 | A1* | 5/2006 | Steffan et al. | 514/406 |
| 2006/0183775 | A1 | 8/2006 | Guglielmotti et al. | |
| 2007/0010555 | A1 | 1/2007 | Alisi et al. | |

FOREIGN PATENT DOCUMENTS

| | | |
|---|---|---|
| EP | 0261964 | 3/1988 |
| EP | 0498466 | 8/1992 |
| EP | 0 726 266 | 8/1996 |
| EP | 0 975 623 B1 * | 6/2002 |
| WO | WO-94/05642 | 3/1994 |
| WO | WO 1998/46589 * | 10/1998 |
| WO | 2004/101548 | 11/2004 |
| WO | WO 2004/101548 * | 11/2004 |
| WO | 2005/013989 | 2/2005 |
| WO | WO 2005/061483 * | 7/2005 |
| WO | WO 2006/055734 * | 5/2006 |
| WO | WO 2008/054748 * | 5/2008 |

OTHER PUBLICATIONS

Harada et al. (Chem. Pharm. Bull. (1995), 43(11); p. 1912-1930.*
Dorwald, F. Zaragoza. Side Reactions in Organic Synthesis: a Guide to Successful Synthesis Design, Weinheim: Wiley-Vch Verlag GmbH & Co. KGaA, 2005, Preface.*
Huang et al. (Bioorganic and Medicinal Chemistry, 14 (2006), 528-536).*
Chem. Pharm. Bull. (1995) 43(11), 1912-1930.
Leysen J.E., Niemegeers C.J., Van Nueten J.M., Laduron P.M. (1982) "[3H]-Ketanserin, a selective 3H-ligand for serotonin2 receptor binding sites. Binding properties, brain distribution, and functional role." Molecular Pharmacology 21: 301-314.
Sztanke K., Fidecka S., Kedzierska E., Karczmarzyk Z., Pihlaja K., Matosiuk D. (2005) "Antionciceptive activity of new imidazole carbonyl derivitives. Part 4. Synthesis and pharmacological activity of 8-aryl-3,4-dioxo-2H,8H-6,7-dihydrimidazo[2, 1c] [1,2,4]triazine." Eur. J. Med. Chem. 40: 127-134.
Corne S.J., Pickering R.W., Warner B.T. (1963) "A method for assessing the effects of drugs on the central actions of 5-hydroxytryptamine." Br. J. Pharmacol. Chemother. 20: 106-120.
Gazzetta Chimica Italiana (1963) 93, 3-14.
Acta Chemica Scandinava (1967), 21 (1), 53-62].
Boess F.G., Steward L.J., Steele J.A., Liu D., Reid J., Glencorse T.A. and Martin I.L. (1997) "Analysis of the ligand binding site of the 5-HT3 receptor using site-directed muta-genesis: importance of glutamate 106." Neuropharmacology 36: 637-647.
Bonhaus D.W., Bach C., De Souza A., Salazar F.H., Matsuoka B.D., Zuppan P., Chan H.W., Eglen R.M. (1995) "The pharmacology and distribution of human 5-hydroxytryptamine2B (5- HT2B) receptor gene products: comparison with 5-HT2A and 5-HT2C receptors." Br.

(Continued)

*Primary Examiner* — Noble Jarrell
*Assistant Examiner* — Valerie Rodriguez-Garcia
(74) *Attorney, Agent, or Firm* — Oblon, Spivak, McClelland, Maier & Neustadt, L.L.P.

(57) ABSTRACT

2-Alkyl-indazole compound and its pharmaceutically acceptable salts of acid addition, method and intermediates for preparing them, a pharmaceutical composition containing them and use of the latter. The 2-alkyl-indazole compound has the following general formula (I) in which R1, R2, R3, R4, R6, R7, X, Y, W, n, p, and m have the meanings stated in the description.

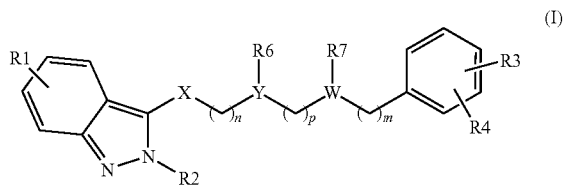

8 Claims, 1 Drawing Sheet

(56) References Cited

OTHER PUBLICATIONS

Gu H., Wall S. and Rudnick G. (1994) "Stable expression of biogenic J. Pharmacol. 115(4): 622-628 —.

Saucier C., Albert P.R. (1997) "Identification of an endogenous 5-hydroxytryptamine2A receptor in NIH-3T3 cells: agonist-induced down-regulation involves decreases in receptor RNA and number." J. Neurochem. 68(5): 1998-2011.

Cheng Y. And Prussof W.H. (1973) "Relationship between the inhibition constant (Ki) and the concentration of inhibitor which causes 50 percent inhibition (150) of an enzyme reaction." Biochem. Pharmacol. 22: 3099-3108.

Grossman C.J., Kilpatrick G.J. and Bunce K.T. (1993) "Development of a radioligand binding assay for 5-HT4 receptors in guinea-pig and rat brain." Br. J. Pharmacol. 109: 618-624. amine transporter reveals differences in inhibitor sensitivity, kinetics, and ion dependence." J. Biol. Chem. 269(10): 7124-7130.

Heuring R.E. and Peroutka S.J. (1987) "Characterization of a novel 3H-5-hydroxytryptamine bin-ding site subtype in bovine brain membranes." J. Neurosci. 7(3): 894-903.

Hoyer D., Engel G. and Kalkman H.O. (1985) "Characterization of the 5-HT1B recognition site in rat brain: binding studies with (-)[125I]iodocyanopindolol." Eur. J. Pharmacol. 18: 1-12.

Martin G.R. and Humphrey P.P.A. (1994) "Receptor for 5-hydroxytryptamine: current perspectives on classification and nomenclature." Neuropharmacol. 33: 261-273.

May J.A., McLaughlin M.A., Sharif N. A., Hellberg M.R. and Dean T.R. (2003) "Evaluation of the ocular hypotensive response of serotonin 5-HT1A and 5-HT2 receptor ligands in conscious ocular hypertensive cynomolgus monkeys." J. Pharmacol. Exp. Ther. 306(1): 301-309.

Mialet J., Berque-Bestel I., Eftekhari P., Gastineau M., Giner M., Dahmoune Y., DonzeauGouge P., Hoebeke J., Langlois M., Sicsic S., Fischmeister R. and Lezoualc'h F. (2000) "Isolation of the serotoninergic 5-HT4(e) receptor from human heart and comparative analysis of its pharmacological profile in C6-glial and CHO cell lines." Br. J. Pharmacol. 129: 771-781.

Millerk W.E., Fletcher P.W. and Teitler M. (1992) "Membrane-bound and solubilized brain 5-HT3 receptor: improved radioligand bin-ding assay using bovine area postrema or rat cortex and the radioligand [3H]GR65630, [3H]BRL43694, and [3H]LY278584." Synapse 11: 58-66.

Monsma F.J. Jr, Shen Y., Ward R.P., Hamblin M.W. and Sibley D.R. (1993) "Cloning and expression of a novel serotonin receptor with high affinity for tricyclic psychotropic drugs." Mol. Pharrnacol. 43: 320-327.

Rees S., den Daas I., Foord S., Goodson S., Bull D., Kilpatriele G. and Lee M. (1994) "Cloning and characterization of the human 5-HT5A serotonin receptor." FEBS Lett. 355: 242-246.

Roth B.L, Craigo S.C., Choudhary M.S., Uluer S., Monsma F.J. Jr, Shen Y., Meltzer H.Y. and Sibley D.R. (1994) "Binding of typical and atypical antipsychotic agents to 5- hydroxytryptamine-6 and 5-hydroxytryptamine-7 receptors." J. Pharmacol. Exp. Ther. 268: 1403-1410.

Shearman L.P., McReynolds A.M., Zhou F.C., Meyer J.S. (1998) "Relationship between [125I]RTI-55-labeled cocaine binding sites and the serotonin transporter in rat placenta." Am. J. Physiol. 275(6 Pt 1): C1621-1629.

Shen Y., Monsma F.J. Jr, Metcalf M.A., Jose P.A., Hamblin M.W. and Sibley D.R. (1993) "Molecular cloning and expression of a 5-hydroxytryptamine 7 serotonin receptor subtype." J. Biol. Chem. 268: 18200-18204.

Wolf W.A. and Kuhn D.M. (1992) "Role of essential sulfhydryl groups in drug interactions at the neuronal 5-HT transporter. Differences between amphetamines and 5-HT uptake inhibitors." J. Biol. Chem. 267(29): 20820-20825.

Wolf W.A. and Schutz J.S. (1997) "The serotonin 5-HT2C receptor is a prominent serotonin receptor in basal ganglia: evidence from functional studies on serotonin-mediated phosphoinositide hydrolysis." J. Neurochem. 69: 1449-1458.

Salazar et al., "Rearrangement of N-(Alkylamino)azoles in Acid Media: A New Entry to C-Amino-N-substituted Azoles" J. Org. Chem., vol. 57, No. 5, (1992), pp. 1563-1567, XP002451039, p. 1564; compound 4I.

Bonhaus D.W., et al. (1995) Br. J. Pharmacol., 115(4): 622-628.

Saucier C., et al. (1997) J. Neurochem., 68(5): 1998-2011.

Grossman C.J., et al. (1993) Br. J. Pharmacol., 109: 618-624.

Elguero J.; in Comprehensive Heterocyclic Chemistry, Katritzky A. R., Ed., Pergamon Press (1984), vol. 5, pp. 167-181.

Elguero J., et al., Bull. Soc. Chim. Fr., (1966) 2075-2084.

Mauret P., et al., Bull. Soc. Chim. Fr., (1975) 1675-1678.

Silvestrini B., et al., Progr. Med. Chem., (1984) 21, 111-135.

Sagi G., et al., J. Med. Chem., (1992) 35, 4549-4556.

Kohlraush K. W. F., et al., Ber. Dtsch. Chem. Ges., (1940) 73, 162-166.

Catalan J., et al., J. Chem. Soc. Perkin Trans. 2, (1996) 57-60.

Fabian W. M. F., Z. Naturforsch Part A, (1990) 45, 1328-1334.

J. A. Mar.., Advanced Organic Chemistry, $2^{nd}$ ed., McGraw-Hill Book Company, NY, pp. 71-74 (1977).

\* cited by examiner

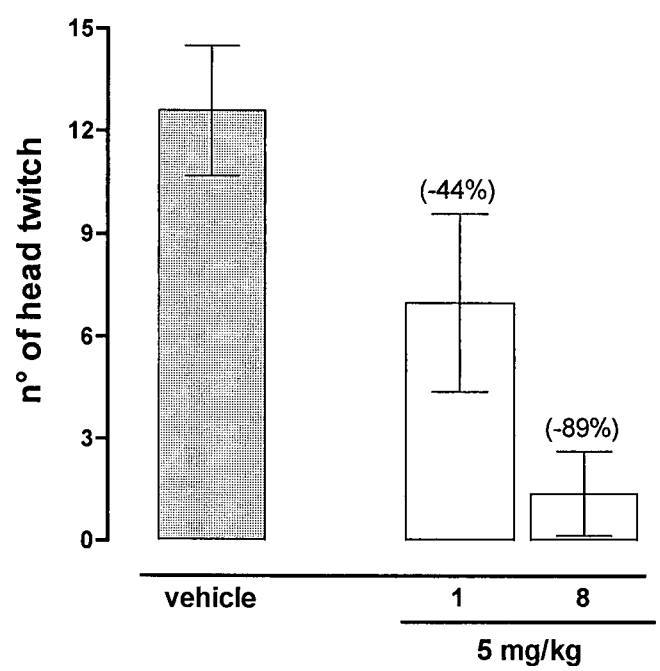

2-ALKYL-INDAZOLE COMPOUNDS FOR THE TREATMENT OF CERTAIN CNS-RELATED DISORDERS

CROSS REFERENCES TO RELATED APPLICATIONS

This application is a 371 of International Patent Application No. PCT/EP07/10000, filed on Nov. 19, 2007, and claims priority to Italian Patent Application No. MI2006 A 002230, filed on Nov. 22, 2006.

The present invention relates to a 2-alkyl-indazole compound, a method and intermediates for preparing it, a pharmaceutical composition containing it and the use of the latter.

In particular, the present invention relates to a 2-alkyl-indazole compound having selective affinity for the $5\text{-}HT_2$ receptor or for other serotonin receptors such as the $5\text{-}HT_1$, $5\text{-}HT_3$, $5\text{-}HT_4$, $5\text{-}HT_5$, $5\text{-}HT_6$ and $5\text{-}HT_7$ receptors. With regard to the various $5\text{-}HT_2$ receptor subtypes, the compounds of the present invention have selective affinity for the $5\text{-}HT_{2A}$ receptor or for the $5\text{-}HT_{2B}$ receptor and generally display preferential affinity for the $5\text{-}HT_{2A}$ receptor compared with the $5\text{-}HT_{2C}$ receptor.

Even more particularly, the present invention relates to a compound that can be used in the treatment of some pathologies that involve the $5\text{-}HT_{2A}$ receptor, for example some disorders of the central nervous system such as sleep disorders, schizophrenia and anxiety, as well as disorders of the smooth muscles or of the gastrointestinal system or of the cardiovascular system.

The serotonin 2A receptor ($5\text{-}HT_{2A}$) is a receptor coupled to protein G, present in many species and widely distributed in the human body. The process of transmission of the signal resulting from receptor activation is not entirely clear. It is known that activation of this receptor, via the protein G coupled to it, leads to the activation of various enzymes such as phospholipase C (with consequent hydrolysis of phosphatidylinositol diphosphate and production of inositol triphosphate) or phospholipase A2 (which leads to the release of arachidonic acid). The receptor response leads, moreover, to a flux of calcium ions ($Ca^{2+}$) into the cell and to activation of functional proteins such as protein kinase C. The receptor is present in the central nervous system, in the cells of the vascular and gastrointestinal smooth muscles and in the platelets.

Now, a 2-alkyl-indazolamide compound having preferential affinity for the $5\text{-}HT_{2A}$ receptor has been found.

This biological activity differs markedly from that of known 2-alkyl-indazole compounds described as pesticides (aryl or ether-aryl 2-alkyl-indazolamides, WO 94/05642), as insecticides (pyridine compounds of 2-methyl-indazolamide, EP-A-0 726 266) or as CRF-1 receptor antagonists (7-aryl or 7-ether-aryl-2-alkyl-indazolamide, US 2004/0 110 815).

This biological activity also differs from that of 1-alkyl-indazole compounds with analgesic activity (WO 04/101548).

Moreover, the compounds of the present invention have a structure that is notably different from the known compounds with preferential affinity for the $5\text{-}HT_{2A}$ receptor and that have reached clinical phases of development, for example EMD-281014 (7-{4-[2-(4-fluoro-phenyl)-ethyl]-piperazine-1-carbonyl}-1H-indole-3-carbonitrile hydrochloride) in phase I for insomnia and MDL-100907 ((R)-(+)-(2,3-dimethoxy-phenyl)-{1-[2-(4-fluoro-phenyl)-ethyl]-piperidin-4-yl}-methanol) in phase II for insomnia.

A first aspect of the present invention relates to a 2-alkyl-indazole compound of general formula (I):

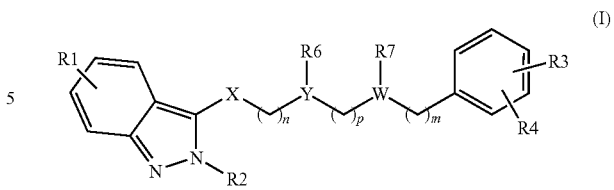

where
X is —C(O)N(R5)- or —N(R5)C(O)—;
Y is CH or N;
W is CH or N;
provided that at least one of Y and W is a nitrogen atom;
n is an integer selected from 0, 1, 2 and 3;
m is an integer selected from 0, 1, 2 and 3;
p is an integer selected from 0, 1 and 2;
R1 is H, $C_{1-3}$ alkyl, $C_{1-3}$ alkoxy, $C_{1-3}$ alkyl-CO—, COOH, R'R"NCO—, R'R"NSO$_2$—, R'SO$_2$—, halogen, R'R"N— or R'CON(R")—;
R2 is linear or branched $C_{1-6}$ alkyl, $C_{1-3}$ alkyl-$C_{1-3}$ alkoxy, aryl-$C_{1-3}$ alkyl in which the aryl group can be substituted with 1 or 2 substituents selected from halogen, $C_{1-3}$ alkyl and $C_{1-3}$ alkoxy;
R3 and R4, which may be the same or different, are H, hydroxy, $C_{1-3}$ alkyl, $C_{1-3}$ alkoxy, R'R"N—, nitro, halogen, trifluoromethyl or R'CON(R")—;
R5 is H, $C_{1-3}$ alkyl, $C_{1-3}$ alkoxy or, together with R6, forms a 5- or 6-membered saturate ring selected from the group comprising pyrrolidine, imidazoline, pyrazolidine, piperidine and piperazine;
R6, together with R5 or R7, forms a 5- or 6-membered saturate ring selected from the group comprising pyrrolidine, imidazoline, pyrazolidine, piperidine and piperazine;
R7 is H, linear or branched $C_{1-6}$ alkyl, aryl-$C_{1-3}$ alkyl, in which the aryl group can be substituted with 1 or 2 substituents selected from halogen, $C_{1-3}$ alkyl, hydroxy, $C_{1-3}$ alkoxy, nitro, trifluoromethyl and R'R"N—, or R7, together with R6, forms a 5- or 6-membered saturate ring selected from the group comprising pyrrolidine, imidazoline, pyrazolidine, piperidine and piperazine;
R' and R", which may be the same or different, are H or $C_{1-3}$ alkyl;
and their salts of addition with pharmaceutically acceptable organic and inorganic acids.

Typical examples of pharmaceutically acceptable acids are: oxalic, maleic, methanesulphonic, paratoluenesulphonic, succinic, citric, tartaric, lactic, hydrochloric, phosphoric and sulphuric.

Preferably, when X is —C(O)N(R5)-,
Y is CH or N;
W is CH or N;
provided that at least one of Y and W is a nitrogen atom;
n is an integer selected from 1, 2 and 3;
m is an integer selected from 0, 2 and 3;
p is an integer selected from 1 and 2;
R1 is H, methyl or methoxy;
R2 is methyl, ethyl, isopropyl or methoxyethyl;
R3 is H, 4-hydroxy, 4-methoxy, 3-chloro or 4-fluoro;
R4 is H or 2-fluoro;
R5 is H, methyl, methoxy or, together with R6, forms a 6-membered saturate ring selected from the group comprising pyrrolidine, imidazoline, pyrazolidine, piperidine and piperazine;

R6, together with R5 or R7, forms a 6-membered saturate ring selected from the group comprising pyrrolidine, imidazoline, pyrazolidine, piperidine and piperazine;

R7 is H, ethyl, phenylethyl, 4-fluorophenylethyl, 2,4-difluorophenylethyl or, together with R6, forms a 6-membered saturate ring selected from the group comprising pyrrolidine, imidazoline, pyrazolidine, piperidine and piperazine.

Preferably, when X is —N(R5)C(O)—,
Y is CH;
W is N;
n is an integer selected from 0 and 1;
m is 2;
p is 2;
R1 is H, methyl or methoxy;
R2 is methyl, ethyl, isopropyl or methoxyethyl;
R3 is H, 4-hydroxy, 4-methoxy, 3-chloro or 4-fluoro;
R4 is H or 2-fluoro;
R5 is H, methyl, or methoxy;
R6, together with R7, forms a 6-membered saturate ring selected from the group comprising pyrrolidine, imidazoline, pyrazolidine, piperidine and piperazine;
R7, together with R6, forms a 6-membered saturate ring selected from the group comprising pyrrolidine, imidazoline, pyrazolidine, piperidine and piperazine.

Even more preferably, X is —C(O)N(R5)-, Y is CH; W is N; n is an integer selected from 1 and 2; m is 2; p is an integer selected from 1 and 2; R1 is H or methoxy; R2 is methyl or methoxyethyl; R3 is H, 4-hydroxy, 4-methoxy or 4-fluoro; R4 is H or 2-fluoro; R5 is H or, together with R6, forms a 6-membered saturate ring selected from the group comprising pyrrolidine, imidazoline, pyrazolidine, piperidine and piperazine; R6, together with R5 or R7, forms a 6-membered saturate ring selected from the group comprising pyrrolidine, imidazoline, pyrazblidine, piperidine and piperazine; R7 is H, ethyl, or, together with R6, forms a 6-membered saturate ring selected from the group comprising pyrrolidine, imidazoline, pyrazolidine, piperidine and piperazine.

A second aspect of the present invention relates to a method for preparing a 2-alkyl-indazole compound of general formula (I) and its salt of acid addition with pharmaceutically acceptable inorganic and organic acids, characterized in that it comprises:

1a) the condensation of an amine of formula (II)

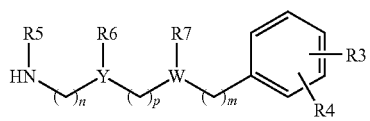

(II)

where
Y, W, R3, R4, R5, R6, R7, n, m and p have the meanings stated previously in relation to the compound of formula (I),
with a derivative of an indazolecarboxylic acid of formula (III)

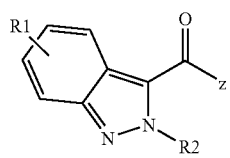

(III)

where
R1 and R2 have the meanings stated previously in relation to the compound of formula (I), and
Z is selected from the group comprising a halogen atom, preferably Cl or Br, an OR and OC(O)R group, where R is a linear or branched alkyl group, having from 1 to 6 carbon atoms,
to give a 2-alkyl-indazole compound of general formula (I); or 1b) the reaction of an amine of general formula (IV):

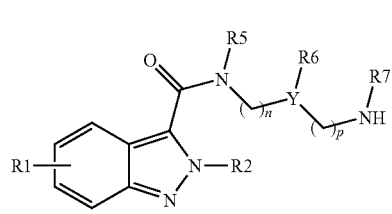

(IV)

where
R1, R2, R5, R6, R7, Y, n and p have the meanings stated previously in relation to the compound of formula (I),
with a compound of general formula (V):

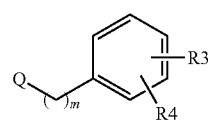

(V)

in which
R3, R4 and m have the meanings stated previously in relation to the compound of formula (I), and
Q is a leaving group selected from the group comprising a halogen atom, preferably Cl or Br, a mesylate group (MeSO$_3$—) and a tosylate group (p-MePhSO$_3$—),
to give a 2-alkyl-indazole compound of general formula (I); or 1c) the condensation of an amine of general formula (VI):

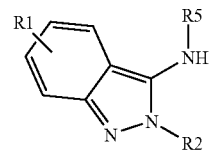

(VI)

where
R1, R2 and R5 have the meanings stated previously in relation to the compound of formula (I),
with a derivative of a carboxylic acid of general formula (VII):

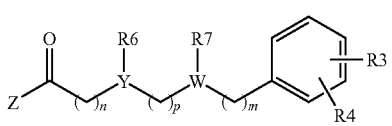

(VII)

where

R3, R4, R6, R7, Y, W, n, m, and p have the meanings stated previously in relation to the compound of formula (I), and Z has the meanings stated previously in relation to the compound of formula (III)

to give a 2-alkyl-indazole compound of general formula (I); and 2) the possible formation of a salt of acid addition of a 2-alkyl-indazole compound of general formula (I) thus obtained with a pharmaceutically acceptable organic or inorganic acid.

Stage 1(a) can be carried out by conventional techniques. For example, an amine of formula (II) is reacted with an acyl halide of formula (III) in which Z is, preferably, a chlorine atom, optionally in the presence of a suitable base. Typical examples of suitable bases are triethylamine and diisopropylethylamine. Advantageously, the reaction is carried out in the presence of a suitable diluent at a temperature from 0 to 140° C., for a time from 0.5 to 24 hours. Preferably, the reaction temperature ranges from 10 to 60° C., whereas the reaction time is from 1 to 12 hours. Typically, the diluent used is aprotic, polar or apolar. Examples of suitable apolar aprotic diluents are aromatic hydrocarbons such as toluene and xylene. Examples of suitable polar aprotic diluents are dichloromethane and N,N-dimethylformamide. Preferably, an apolar aprotic diluent is used.

The compound obtained in stage 1(a) can also be purified by conventional techniques such as flash chromatography and crystallization.

Stage 1(b) can also be carried out by conventional techniques. For example, an amine of formula (IV) is reacted with a compound of formula (V) in which Q is, preferably, a bromine atom or a methanesulphonyl group, optionally in the presence of a suitable base. Typical examples of suitable bases are potassium carbonate and sodium carbonate. Preferably, the reaction is carried out in the presence of a suitable diluent at a temperature from room temperature to 160° C. and for a time from 1 to 48 hours. Preferably, the reaction temperature ranges from room temperature to 100° C., whereas the reaction time is from 6 to 24 hours. Typically, the diluent used is polar, protic or aprotic. Examples of suitable polar protic diluents are alcohols such as ethanol, whereas an example of a suitable polar aprotic diluent is acetone.

The compound obtained in stage 1(b) can also be purified by conventional techniques such as flash chromatography and crystallization.

Stage 1(c) can also be carried out by conventional techniques. For example, an amine of formula (VI) is reacted with an acyl halide of formula (VII) in which Z is, preferably, a chlorine atom, optionally in the presence of a suitable base. Typical examples of suitable bases are triethylamine and diisopropylethylamine. Advantageously, the reaction is carried out in the presence of a suitable diluent at a temperature from 0 to 140° C., for a time from 0.5 to 24 hours. Preferably, the reaction temperature ranges from 10 to 60° C., whereas the reaction time is from 1 to 12 hours. Typically, the diluent used is aprotic, polar or apolar. Examples of suitable apolar aprotic diluents are the aromatic hydrocarbons such as toluene and xylene. Examples of suitable polar aprotic diluents are dichloromethane and N,N-dimethylformamide. Preferably, an apolar aprotic diluent is used.

The compound obtained in stage 1(c) can also be purified by conventional techniques such as flash chromatography and crystallization.

The formation of a salt of acid addition of a 2-alkyl-indazole compound of general formula (I) with a pharmaceutically acceptable organic or inorganic acid can also be carried out by conventional techniques. For example, it can be carried out by dissolving the compound of formula (I) in a suitable diluent and treating the solution thus obtained with an organic or aqueous solution of the acid of interest. Typical examples of suitable diluents are ethanol, isopropanol, ethyl acetate and diethyl ether. The salt that forms can then be separated by conventional techniques and, if applicable, purified by crystallization.

Some intermediates of formula (II), (IV), and (VI) are novel, and they therefore constitute a further aspect of the present invention.

In particular, the following are novel:

(a) the compounds of formula (II):

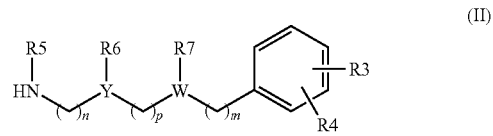

(II)

in which

R3 and R4, which may be the same or different, are H, hydroxy, $C_{1-3}$ alkyl, $C_{1-3}$ alkoxy, R'R"N—, nitro, halogen, trifluoromethyl or R'CON(R")—, provided, however, that R3 and R4 are not both an H atom, R5 is $C_{1-3}$ alkyl, R6 and R7, together, form a 5- or 6-membered saturate ring selected from the group comprising pyrrolidine, imidazoline, pyrazolidine, piperidine and piperazine, Y is CH, W is N, n is an integer selected from 1, 2 and 3, p is an integer selected from 0 and 1, m is 2.

R' and R", which may be the same or different, are H or $C_{1-3}$ alkyl;

(b) the compounds of formula (IV):

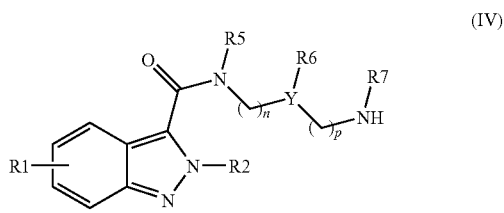

(IV)

in which

R1, R2, R5, R6, R7, Y, n, and p have the meanings stated previously in relation to the compound of formula (I);

(c) the compounds of formula (VI):

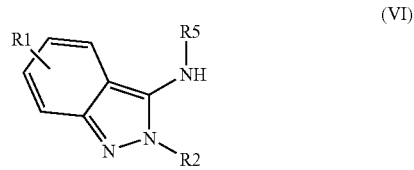

(VI)

in which both R1 and R2 have the meanings stated previously in relation to the compound of formula (I), and R5 is H, $C_{1-3}$ alkyl or $C_{1-3}$ alkoxy.

The amine (II) can be prepared by conventional methods, for example as described in the applicant's patent application WO 04/101548.

When R5 is different from H, amine (II) is advantageously prepared (Scheme 1) by amidation of an amine (XI) to give a compound (XII) and then exhaustive reduction of compound (XII) to give the amine (II).

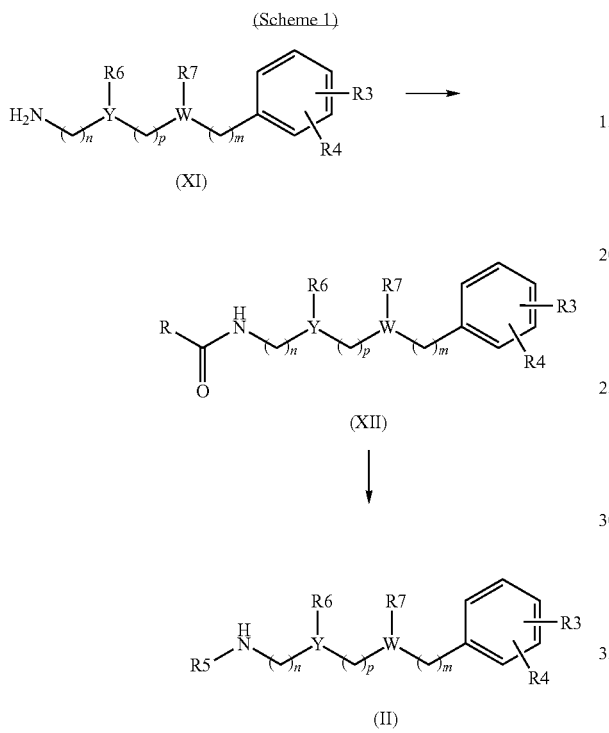

Most of the intermediates of general formula (XI) and (XII) are novel.

In particular, the following intermediates collectively represented by the following general formula (XX) are novel and thus constitute a further object of the present invention:

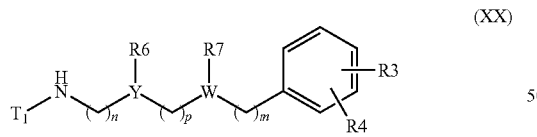

where
$T_1$ is H, $C_{1-3}$ alkyl or $C_{1-3}$ alkoxy or R—CO in which R is H or $C_{1-3}$ alkyl,
R3 and R4, which may be the same or different, are H, hydroxy, $C_{1-3}$ alkyl, $C_{1-3}$ alkoxy, R'R"N—, nitro, halogen, trifluoromethyl or R'CON(R")—, where R' and R", which may be the same or different, are H or $C_{1-3}$ alkyl; provided, however, that R3 and R4 are not both an H atom,
R6 and R7, together, form a 5- or 6-membered saturate ring selected from the group comprising pyrrolidine, imidazoline, pyrazolidine, piperidine and piperazine,
Y is CH,
W is N,
n is an integer selected from 1, 2 and 3,
p is an integer selected from 0, 1 and 2, and
m is 2.

The indazolecarboxylic acid (III) can be prepared by conventional methods. For example by alkylating an ester of an indazole-3-carboxylic acid (VIII) with an alkyl halide (IX) according to Chem. Pharm. Bull. (1995) 43(11), 1912-1930, then separating the 2-alkylated compound (X) from the reaction mixture by chromatography, then submitting the 2-alkylated compound (X) to basic hydrolysis and, finally, converting the compound thus obtained to the desired carboxylic compound (III) as shown in the following Scheme 2:

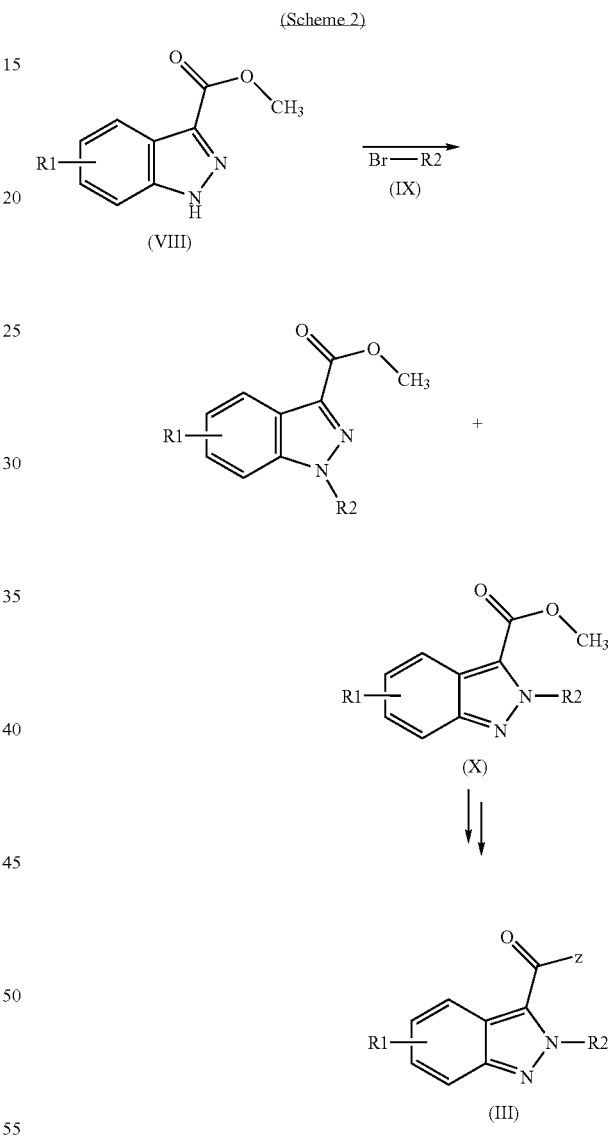

Compound (IV) can be prepared, for example, from an amine (XIII), in which the primary amine group is protected by a protecting group P (Scheme 3) as described for example by Green T. W. and Wuts P. G. M., "*Protective groups in organic synthesis*." John Wiley & Sons Publ. (1991). Then, compound (XIV) thus obtained is reacted with compound (III). Next, the amide that formed (XV) is deprotected, according to the techniques described by Green T. W. and Wuts P. G. M., "*Protective groups in organic synthesis*." John Wiley & Sons Publ. (1991), forming the primary amine (XVI) which is acylated to give amide (XVII) then reduced, as in the procedure described in Scheme 1, to give compound (IV).

(Scheme 3)

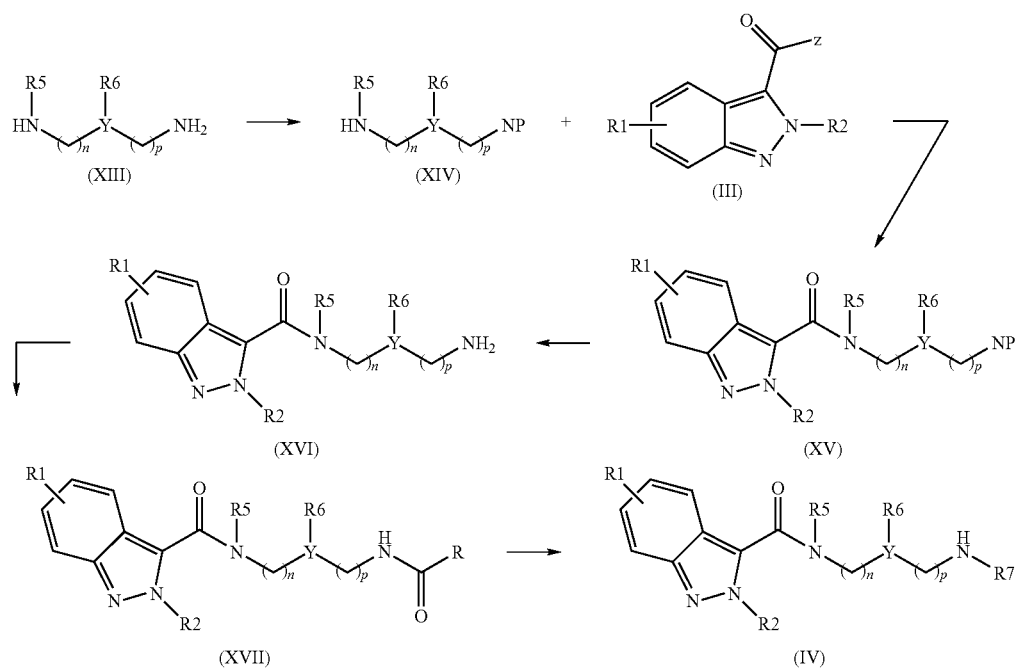

Most of the intermediates of general formula (XV), (XVI) and (XVII) are novel.

In particular, the following intermediates represented collectively by the following general formula (XXX) are novel, and thus constitute a further object of the present invention:

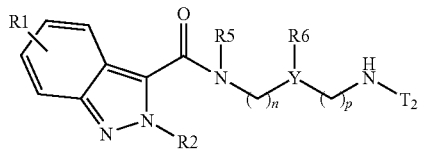

(XXX)

where
R1 and R2 have the meanings stated previously in relation to the compound of formula (I),
$T_2$ is H, a protecting group (P) selected from the group comprising 9-fluorenyl methylcarbamate, tert-butylcarbamate, allylcarbamate, n-benzyl and n-benzylidene, or a group R—CO in which R is $C_{1-3}$ alkyl,
R5 and R6, together, form a 5- or 6-membered saturate ring selected from the group comprising pyrrolidine, imidazoline, pyrazolidine, piperidine and piperazine,
Y is CH,
n is an integer selected from 1, 2 and 3,
p is an integer selected from 0, 1 and 2, and
m is 2.

However, regarding procedure (1c), the amine (VI) can be prepared according to conventional methods, for example those described by Fusco R., "*The chemistry of heterocyclic compounds, Pyrazoles, Pyrazolines, Indazoles and condensed rings.*" (1967) Publ. Wiley N.Y., or by Katritsky A. and Rees C. W., "*Comprehensive heterocyclic chemistry.*" Vol. 5 (1984) Publ. Pergamon Press.

Compound (VII) can also be prepared by conventional methods, for example those described in patent application WO 04/101548.

Another aspect of the present invention relates to a pharmaceutical composition comprising an effective dose of at least one 2-alkyl-indazole compound of formula (I) or of its salt with a pharmaceutically acceptable organic or inorganic acid and at least one pharmaceutically acceptable excipient.

Preferably, the pharmaceutical composition of the present invention is prepared in suitable dosage forms comprising an effective dose of at least one 2-alkyl-indazole compound of formula (I) or of a salt thereof with a pharmaceutically acceptable organic or inorganic acid and at least one pharmaceutically acceptable excipient.

Typical examples of pathological states that might benefit from treatment with the pharmaceutical composition according to the present invention are some disorders of the central nervous system, such as sleep disorders, schizophrenia and anxiety, as well as disorders of smooth muscles both of the gastrointestinal system and of the cardiovascular system.

Therefore, a further aspect of the present invention relates to the use of the aforementioned pharmaceutical composition for treating a pathological state selected from the group comprising sleep disorders, schizophrenia, anxiety, disorders of the smooth muscles both of the gastrointestinal system and of the cardiovascular system.

Examples of suitable dosage forms are tablets, capsules, coated tablets, granules, solutions and syrups for oral administration; medicated patches for transdermal administration; suppositories for rectal administration and injectable sterile solutions.

Other suitable dosage forms are those with sustained release and those based on liposomes for oral, injectable or transdermal administration.

The dosage forms can also contain other traditional ingredients such as: preservatives, stabilizers, surfactants, buffers, salts for regulating osmotic pressure, emulsifiers, sweeteners, colorants, flavourings and the like.

If called for by special therapeutic requirements, the pharmaceutical composition of the present invention can contain other pharmacologically active ingredients, whose simultaneous administration should be beneficial.

The amount of 2-alkyl-indazole compound of formula (I) or of its pharmaceutically acceptable salt of acid addition in the pharmaceutical composition of the present invention can vary over a wide range depending on known factors, for example the type of pathology, the severity of the disease, the patient's body weight, the dosage form, the chosen route of administration, the number of administrations per day and the efficacy of the selected 2-alkyl-indazole compound of formula (I). However, the optimum amount can be determined by a person skilled in the art easily and routinely.

Typically, the amount of 2-alkyl-indazole compound of formula (I) or of its pharmaceutically acceptable salt of acid addition in the pharmaceutical composition of the present invention will be such as to ensure a level of administration from 0.0001 to 100 mg/kg/day. Preferably, the level of administration is from 0.001 to 50 mg/kg/day, even more preferably from 0.01 to 10 mg/kg/day.

The dosage forms of the pharmaceutical composition of the present invention can be prepared by techniques that are familiar to a pharmaceutical chemist, and comprise mixing, granulation, compression, dissolution, sterilization and the like.

The pharmacological properties of the compounds of formula (I) according to the present invention were evaluated by the methods described later, in the sections Tests A, B and C.

Briefly, the affinity for the rat 5-$HT_{2A}$ receptor was demonstrated by the standard methodology in: Leysen J. E., Niemegeers C. J., Van Nueten J. M., Laduron P. M. (1982) "[3H]-Ketanserin, a selective 3H-ligand for serotonin2 receptor binding sites. Binding properties, brain distribution, and functional role." Molecular Pharmacology 21: 301-314. (Test A).

The values of the affinity of some compounds of formula (I) according to the present invention for the 5-HT2A receptor are shown in Table 1, in which the affinity is greater for a higher value of pKi.

TABLE 1

| Compound (No.) | 5-$HT_{2A}$ (pKi) |
| --- | --- |
| 8 | 7.80 |
| 1 | 7.49 |
| 3 | 7.32 |
| 4 | 7.32 |
| 7 | 7.04 |
| 10 | 6.58 |
| 9 | 6.20 |
| 2 | 6.09 |
| 5 | 5.80 |

The selective affinity of the compounds of formula (I) according to the present invention for other receptors or systems for transporting and incorporating serotonin was also determined using standard methodology (Test B).

These tests measured the percentage inhibition induced by the compounds of formula (I) according to the present invention at a concentration of 1 µM for the receptors: 5-$HT_{1A}$, 5-$HT_{1B}$, 5-$HT_{1D}$, 5-$HT_{2b}$, 5-$HT_3$, 5-$HT_4$, 5-$HT_{4(b)}$, 5-$HT_{5(A)}$, 5-$HT_6$ and 5-$HT_7$. In addition, the percentage inhibition induced by the compounds of formula (I) according to the present invention at 1 µM on the serotonin transport system and at 10 µM on the cellular system for incorporating serotonin was measured.

In all cases, the compounds of formula (I) according to the present invention induced a percentage inhibition, at the concentration used, of less than 50%.

The preferential affinity of the compounds of formula (I) according to the present invention for the 5-$HT_{2A}$ receptor compared with the 5-$HT_{2c}$ receptor was also determined using standard methodology (Test B). These tests measured the percentage inhibition induced by the compounds of formula (I) according to the present invention at six different concentrations, from which the pKi values of the compounds in relation to the individual receptors were obtained.

The values of affinity of some compounds of formula (I) according to the present invention for the 5-$HT_{2A}$ and 5-$HT_{2c}$ receptors of human recombinant cells are shown in Table 2, in which the affinity is greater for a higher value of pKi.

TABLE 2

| Compound (No.) | (h)5-$HT_{2a}$ (pKi) | (h)5-$HT_{2c}$ (pKi) |
| --- | --- | --- |
| 8 | 8.79 | 7.27 |
| 1 | 8.58 | 7.05 |
| 3 | 8.68 | 6.83 |

Moreover, the compounds of formula (I) according to the present invention were assessed in vivo in the "head twitch" model in the mouse (Test C). This is a standard test for detecting any interactions with the serotoninergic system as described in Sztanke K., Fidecka S., Kedzierska E., Karczmarzyk Z., Pihlaja K., Matosiuk D. (2005) "Antionociceptive activity of new imidazole carbonyl derivatives. Part 4. Synthesis and pharmacological activity of 8-aryl-3,4-dioxo-2H, 8H-6,7-dihydrimidazo[2,1c][1,2,4]triazine." Eur. J. Med. Chem. 40: 127-134, and in Come S. J., Pickering R. W., Warner B. T. (1963) "A method for assessing the effects of drugs on the central actions of 5-hydroxytryptamine." Br. J. Pharmacol. Chemother. 20: 106-120.

In this test, the compounds under investigation induced a decrease in the number of "head twitches" relative to animals treated with methylcellulose (MTC) alone, thus demonstrating the capacity for antagonizing the serotoninergic effects induced by the administration of 5-hydroxytryptophan (5-HTP). The inhibition values obtained in the "Head Twitch" test with the test compounds are shown in FIG. 1.

The description that follows is intended for further illustration of the present invention, though without limiting it.

EXAMPLE 1

2-Methyl-N-{[1-(2-phenylethyl)piperidin-4-yl]methyl}-2H-indazole-3-carboxamide hydrochloride hydrate (Compound No. 1)

(Compound I: R1=H, R2=$CH_3$, X=—C(O)N(R5)-, R3=R4=R5=H, n=1, p=2, m=2, Y=CH, W=N, R6+R7=—$CH_2$—$CH_2$—)

1a) Methyl ester of 2-methyl-2H-indazole-3-carboxylic acid (Compound X: R1=H, R2=$CH_3$)

Potassium carbonate (207.1 g; 1.498 mol) and, dropwise, methyl iodide (31 ml; 0.50 mol) were added to a suspension of methyl ester of 1H(2H)-indazole-3-carboxylic acid (74.0 g; 0.499 mol) in acetone (750 ml). The reaction mixture was heated under reflux for 4 h, cooled and filtered. The solvent was removed by evaporation at reduced pressure and the residue was taken up twice in ethyl acetate.

Approximately 80 g of raw compound was thus obtained. The solid was crystallized twice from n-hexane/ethyl acetate, obtaining the methyl ester of 2-methyl-2H-indazole-3-carboxylic acid (50.0 g).

$^1$H-NMR (δ, DMSO-d6): 3.93 (s, 3H); 4.17 (s, 3H); 7.3-7.4 (m, 1H); 7.5-7.6 (m, 1H); 7.7-7.8 (m, 1H); 8.0-8.1 (m, 1H).

1b) Chloride of 2-methyl-2H-indazole-3-carboxylic acid (Compound III; R1=H, R2=CH$_3$, Z=Cl)

Hydrolysis of the methyl ester of 2-methyl-2H-indazole-3-carboxylic acid (1a) (50.0 g; 0.260 mol) was carried out in water (300 ml) containing sodium hydroxide (20.9 g; 0.520 mol). The reaction mixture was boiled under reflux for 2 h, cooled to room temperature and acidified with 2N HCl until precipitation of a white solid ceased. After filtration and stove-drying under vacuum, 45.2 g of 2-methyl-2H-indazole-3-carboxylic acid was obtained, and this was used without further purification in the subsequent reactions.

Thionyl chloride (39 ml; 0.54 mol) was added to a suspension of 2-methyl-2H-indazole-3-carboxylic acid (45.2 g; 0.270 mol) in toluene (350 ml) and the reaction mixture was heated under reflux for 24 h. The solvent was removed by evaporation at reduced pressure. The residue was taken up twice in toluene. 47.0 g of chloride of 2-methyl-2H-indazole-3-carboxylic acid was thus obtained.

$^1$H-NMR (δ, DMSO-d6): 3.97 (s, 3H); 7.3-7.4 (m, 1H); 7.5-7.6 (m, 1H); 7.7-7.8 (m, 1H); 8.0-8.1 (m, 1H).

1c) 1-[1-(2-Phenylethyl)-4-piperidinyl]methanamine (Compound XI: R3=R4=H, R6+R7=—CH$_2$—CH$_2$—, n=1, p=2, m=2)

Benzaldehyde (28.0 g; 0.264 mol) was added, dropwise, to a solution of 4-aminomethylpiperidine (30.2 g; 0.264 mol) in toluene (100 ml). The solution thus obtained was kept stirred at room temperature. After 3 h, the solvent was removed by evaporation at reduced pressure and the residue was taken up twice in toluene. 53.4 g of N-hexahydro-4-pyridinylmethyl-N-phenylmethylidenamine was thus obtained, and was used in subsequent reaction without further purification.

N-Hexahydro-4-pyridinylmethyl-N-phenylmethylidenamine (53.4 g; 0.264 mol) was dissolved in absolute ethanol (500 ml) containing anhydrous potassium carbonate (73.0 g; 0.528 mol) and phenethyl bromide (39.5 ml; 0.290 mol). The reaction mixture thus obtained was boiled under reflux for 24 h. After cooling to room temperature, the suspension was filtered and the solvent was evaporated at reduced pressure. The residue thus obtained was suspended in 3N HCl (200 ml) and stirred at room temperature for 2 h. The acidic aqueous phase was washed 4 times with ethyl acetate and then alkalized to pH approx. 13 with 6N NaOH and extracted with dichloromethane. The organic phase thus obtained was dried over anhydrous Na$_2$SO$_4$ and the solvent was removed by evaporation at reduced pressure.

50.0 g of 1-[1-(2-phenylethyl)-4-piperidinyl]methanamine was thus obtained.

$^1$H-NMR (δ, CDCl$_3$): 1.3-1.4 (m, 5H); 1.7-1.8 (m, 2H); 1.9-2.1 (m, 2H); 2.5-2.6 (m, 4H); 2.7-2.9 (m, 2H); 2.9-3.1 (m, 2H); 7.1-7.3 (m, 5H).

1d) 2-Methyl-N-{[1-(2-phenylethyl)piperidin-4-yl]methyl}-2H-indazole-3-carboxamide hydrochloride hydrate (Compound I: R1=H, R2=CH$_3$, X=—C(O)N(R5)-, R3=R4=R5=H, n=1, p=2, m=2, Y=CH, W=N, R6+R7=—CH$_2$—CH$_2$—)

1-[1-(2-Phenylethyl)-4-piperidinyl]methanamine (1c) (20.3 g; 0.0930 mol) was added to a solution of chloride of 2-methyl-2H-indazole-3-carboxylic acid (1b) (18.0 g; 0.0930 mol) in toluene (100 ml). The reaction mixture was kept stirred at room temperature overnight and then filtered. The solid was taken up in 1N NaOH and extracted with dichloromethane (DCM). The organic phases were combined and then dried over anhydrous Na$_2$SO$_4$, and the solvent was removed by evaporation at reduced pressure.

The raw compound thus obtained was converted to the corresponding hydrochloride by dissolution in ethyl acetate, treatment with an excess of 5N hydrochloric ethanol at room temperature for 3 h, removal of the solvent by evaporation at reduced pressure and crystallization of the solid obtained from ethyl acetate/absolute ethanol. 7.2 g of 2-methyl-N-{[1-(2-phenylethyl)piperidin-4-yl]methyl}-2H-indazole-3-carboxamide hydrochloride hydrate was obtained.

m.p.=130-140° C.

Elemental analysis for C, 23; H, 31; ClN, 4; O, 2

|  | C | H | N | Cl |
|---|---|---|---|---|
| Found % | 64.16 | 7.37 | 12.89 | 8.46 |
| Calculated % | 64.10 | 7.25 | 13.00 | 8.59 |

$^1$H-NMR (δ, DMSO-d6): 1.59-2.10 (m, 5H); 2.80-3.40 (m, 10H); 3.59 (d, J=12 Hz, 2H); 4.31 (s, 3H); 7.15-7.40 (m, 7H); 7.69 (d, J=9 Hz, 1H); 7.84 (d, J=9 Hz, 1H); 8.63 (t, J=6 Hz, 1H); 10.50-10-70 (s broad, 1H).

EXAMPLE 2

N,2-Dimethyl-N-{[1-(2-phenylethyl)piperidin-4-yl]methyl}-2H-indazole-3-carboxamide hydrochloride hemihydrate (Compound No. 2)

(Compound I: R1=H, R2=CH$_3$, X=—C(O)N(R5)-, R3=R4=H, R5=CH$_3$, n=1, p=2, m=2, Y=CH, W=N, R6+R7=—CH$_2$—CH$_2$—)

2a) N,2-Dimethyl-N-{[1-(2-phenylethyl)piperidin-4-yl]methyl}-2H-indazole-3-carboxamide hydrochloride hemihydrate After stirring for 1 h at room temperature, methyl iodide (0.83 ml; 0.013 mol) was added to a suspension of 2-methyl-N-{[1-(2-phenylethyl)piperidin-4-yl]methyl}-2H-indazole-3-carboxamide (1d) (5.0 g; 0.013 mol) and 60% sodium hydride (0.51 g; 0.013 mol) in tetrahydrofuran (THF) (50 ml). The mixture thus obtained was stirred at room temperature for 48 h. Then distilled water was added to remove any excess hydride. The organic phase was separated and concentrated by evaporation at reduced pressure.

The residue obtained was purified using flash chromatography (eluents CHCl$_3$/CH$_3$OH/NH$_3$ in proportions 85/14/1) and converted to hydrochloride by dissolution in ethyl acetate, treatment with an excess of 5N hydrochloric ethanol at room temperature for 3 h and removal of the solvent by evaporation at reduced pressure.

The compound thus obtained was crystallized from ethyl acetate/absolute ethanol. 5.2 g of N,2-dimethyl-N-{[1-(2-phenyl-ethyl)piperidin-4-yl]methyl}-2H-indazole-3-carboxamide hydrochloride hemihydrate was thus obtained.

m.p.=206-207° C.

Elemental analysis for C, 24; H, 33; ClN, 4; O, 2

|  | C | H | N | Cl |
|---|---|---|---|---|
| Found % | 63.70 | 7.44 | 12.26 | 7.82 |
| Calculated % | 63.49 | 7.55 | 12.34 | 7.81 |

$^1$H-NMR (δ, DMSO-d$_6$+D$_2$O): 1.50-2.30 (m, 5H); 2.80-3.80 (m, 14H); 3.01 (s, 3H); 4.15 (s, 3H); 7.10-7.40 (m, 7H); 7.61 (t, J=8 Hz, 1H); 7.69 (d, J=9 Hz, 1H).

EXAMPLE 3

N3-({1-[2-(4-Hydroxyphenyl)ethyl]hexahydro-4-pyridinyl}methyl-2-methyl-2H-3-indazolecarboxamide hydrochloride hydrate (Compound No. 3)

(Compound I: R1=H, R2=CH$_3$, X=—C(O)N(R5)-, R3=4-OH, R4=H, R5=H, n=1, p=2, m=2, Y=CH, W=N, R6+R7=—CH$_2$—CH$_2$—)

3a) 1-(2-(4-Hydroxyphenyl)ethyl)-4-piperidinyl methanamine (Compound XI: R3=4-OH, R4=H, R6+R7=—CH$_2$—CH$_2$—, n=1, p=2, m=2)

Preparation was similar to that described for preparation (1c) starting from N-hexahydro-4-pyridinylmethyl-N-phenyl-methylidenamine (7.5 g, 0.037 mol) and 2-(4-hydroxyphenyl)ethyl bromide (7.5 g; 0.037 mol) [prepared as described in *Acta Chemica Scandinava* (1967), 21 (1), 53-62]. 9.3 g of 1-(2-(4-hydroxyphenyl)ethyl)-4-piperidinylmethanamine was thus obtained.

$^1$H-NMR (δ, CDCl$_3$+D$_2$O): 1.15-1.41 (m, 3H); 1.74 (d, J=9 Hz, 2H); 1.9-2.1 (m, 2H); 2.4-2.6 (m, 4H); 2.65-2.75 (m, 2H); 3.01 (d, J=12 Hz, 2H); 6.75 (d, J=9 Hz, 2H); 7.00 (d, J=9 Hz, 2H).

3b) N3-({1-[2-(4-Hydroxyphenyl)ethyl]hexahydro-4-pyridinyl}methyl-2-methyl-2H-3-indazolecarboxamide hydrochloride hydrate 1-(2-(4-Hydroxyphenyl)ethyl)-4-piperidinylmethanamine (3a) (5.6 g; 0.024 mol) was added in small portions to a solution of chloride of 2-methyl-2H-indazole-3-carboxylic acid (1b) (4.7 g; 0.024 mol) in toluene (100 ml).

The mixture thus obtained was stirred for 18 h at room temperature. Then it was filtered. The residue was purified several times by crystallization from ethyl acetate/absolute ethanol and converted to hydrochloride by dissolution in ethyl acetate, treatment with an excess of 5N hydrochloric ethanol at room temperature for 3 h, and removal of the solvent by evaporation at reduced pressure.

After crystallization from ethyl acetate/absolute ethanol, 5.0 g of N3-({1-[2-(4-hydroxyphenyl)ethyl]hexahydro-4-pyridinyl}methyl)-2-methyl-2H-3-indazolecarboxamide hydrochloride hydrate was obtained.

m.p.=236-238° C.

Elemental analysis for C, 23; H, 29; ClN, 4; O, 2¾; H2O

|  | C | H | N | Cl |
|---|---|---|---|---|
| Found % | 62.43 | 6.96 | 12.58 | 8.06 |
| Calculated % | 62.43 | 6.95 | 12.66 | 8.09 |

$^1$H-NMR (δ, DMSO-d6): 1.5-2.1 (m, 5H); 2.8-3.4 (m, 9H); 3.57 (d, J=11 Hz, 2H); 4.30 (s, 3H); 6.73 (d, J=9 Hz, 2H); 7.06 (d, J=9 Hz, 2H); 7.2-7.3 (m, 1H); 7.3-7.4 (m, 1H); 7.68 (d, J=9 Hz, 1H); 7.84 (d, J=9 Hz, 1H); 8.65(t, J=6 Hz, 1H); 9.2-9.5 (s broad, 1H); 10.4-10.7 (s broad, 1H).

EXAMPLE 4

N-({1-[2-(4-Hydroxyphenyl)ethyl]piperidin-4-yl}methyl)-5-methoxy-2-methyl-2H-indazole-3-carboxamide (Compound No. 4)

(Compound I; R1=5-CH$_3$O, R2=CH$_3$, X=—C(O)N(R5)-, R3=4-OH, R4=H, R5=H, n=1, p=2, m=2, Y=CH, W=N, R6+R7=—CH$_2$—CH$_2$—)

4a) 5-Methoxy-2-methyl-2H-indazole-3-carboxylic acid methyl ester (Compound X: R1=5-CH$_3$O, R2=CH$_3$)

A mixture of 5-methoxy-indazole-3-carboxylic acid [prepared according to Gazzetta Chimica Italiana (1963) 93, 3-14](11.8 g; 0.0610 mol), methanol (200 ml) and sulphuric acid (2 ml) was stirred at room temperature for 4 h. The mixture was then diluted with distilled water. The solid that formed was separated by filtration, dried in a stove (9.6 g) and used without further purification for subsequent reaction.

Potassium hydroxide (3.6 g; 0.064 mol) was added, in small portions, to a suspension containing methyl ester of 5-methoxy-indazole-3-carboxylic acid (9.6 g; 0.047 mol) and methyl iodide (3.4 ml; 0.054 mol) in dimethoxyethane (DME) (50 ml). The reaction mixture was heated under reflux for 18 h and then cooled. The solvent was removed by evaporation at reduced pressure. The solid was taken up in toluene and washed several times with water and 6N NaOH. The solvent was then evaporated at reduced pressure, and the residue obtained was purified by flash chromatography (n-hexane/ethyl acetate=7/3). 5.0 g of 5-methoxy-2-methyl-2H-indazole-3-carboxylic acid methyl ester was thus obtained.

$^1$H-NMR (δ, CDCl$_3$): 3.90 (s, 3H); 4.03 (s, 3H); 4.47 (s, 3H); 7.0-7.1 (dd, J1=9.3 Hz, J2=2.3 Hz, 1H); 7.2-7.3 (d, J=2.3 Hz, 1H); 7.6-7.7 (dd, J1=9.3 Hz, J2=0.7 Hz, 1H).

4b) Chloride of 5-methoxy-2-methyl-2H-indazole-3-carboxylic acid (Compound III: R1=5-CH$_3$O, R2=CH$_3$; Z=Cl)

Sodium hydroxide (1.0 g; 0.025 mol) was added to a suspension of methyl ester of 5-methoxy-2-methyl-2H-indazole-3-carboxylic acid (prepared as described in the previous Example 4a) (2.8 g; 0.013 mol) in distilled water (40 ml). The mixture thus obtained was left to react under reflux for 4 h, cooled and acidified with 2N HCl until precipitation of 5-methoxy-2-methyl-2H-indazole-3-carboxylic acid was completed, and after filtration this was used without further purification in the subsequent reactions.

Thionyl chloride (0.8 ml; 0.01 mol) was added to a flask containing 5-methoxy-2-methyl-2H-indazole-3-carboxylic acid (1.1 g; 0.0050 mol) and toluene (30 ml). The reaction mixture was reacted under reflux for 5 h and, after evaporating the solvent at reduced pressure, the residue was taken up several times in toluene. 1.2 g of chloride of 5-methoxy-2-methyl-2H-indazole-3-carboxylic acid was thus obtained.

$^1$H-NMR (δ, CDCl$_3$): 3.90 (s, 3H); 4.47 (s, 3H); 7.0-7.1 (dd, J1=9.3 Hz, J2=2.3 Hz, 1H); 7.2-7.3 (d, J=2.3 Hz, 1H); 7.6-7.7 (dd, J1=9.3 Hz, J2=0.7 Hz, 1H).

4c) N-({1-[2-(4-Hydroxyphenyl)ethyl]piperidin-4-yl}methyl-5-methoxy-2-methyl-2H-indazole-3-carboxamide 1-(2-(4-Hydroxyphenyl)ethyl)-4-piperidinyl methanamine (3a) (1.25 g; 0.0050 mol) was added in small portions to a suspension of chloride of 5-methoxy-2-methyl-2H-indazole-3-carboxylic acid (4b) (1.2 g; 0.0050 mol) in toluene (30 ml). The mixture thus obtained was left to react for 4 h at room temperature and to reflux for a further 4 h. Then the suspension was cooled and filtered. The solid was purified by crystallization from n-hexane/ethyl acetate.

1.5 g of N-({1-[2-(4-hydroxyphenyl)ethyl]piperidin-4-yl}methyl)-5-methoxy-2-methyl-2H-indazole-3-carboxamide was thus obtained.

m.p.=218-219° C. (decomp.)

$^1$H-NMR (δ, DMSO-d6+D$_2$O): 1.2-1.3 (m, 2H); 1.5-1.8 (m, 1H); 1.73 (d, J=12 Hz, 2H); 1.93 (t, J=12 Hz, 2H); 2.3-2.7 (m, 4H); 2.93 (d, J=11 Hz, 2H); 3.26 (d, J=6 Hz, 2H); 3.82 (s, 3H); 4.24 (s, 3H); 6.66 (d, J=9 Hz, 2H); 6.9-7.1 (m, 4H); 7.59 (d, J=9 Hz, 1H); 8.40 (t, J=6 Hz, 1H).

MS shows 423 (MH$^+$) base peak.

EXAMPLE 5

N-({1-[2-(4-Methoxyphenyl)ethyl]piperidin-4-yl}methyl)-2-methyl-2H-indazole-3-carboxamide hydrochloride (Compound No. 5)

(Compound I: R1=H, R2=CH$_3$, X=—C(O)N(R5)-, R3=4-CH$_3$O—, R4=H, R5=H, n=1, p=2, m=2, Y=CH, W=N, R6+R7=—CH$_2$—CH$_2$—)

5a) 1-[2-(4-Methoxyphenyl)ethyl]-4-piperidinyl-methanamine (Compound XI: R3=4-CH$_3$O, R4=H, R6+R7=—CH$_2$—CH$_2$—, n=1, p=2, m=2)

The compound was obtained in a similar manner to that described for preparation 1c) starting from N-hexahydro-4-pyridinylmethyl-N-phenylmethylidenamine (12.9 g; 0.0631 mol) and 2-(4-methoxyphenyl) ethyl bromide (15.0 g; 0.0698 mol) [prepared as described in *Acta Chemica Scandinava* (1967), 21 (1), 53-62].

5.0 g of 1-[2-(4-methoxyphenyl)ethyl]-4-piperidinyl-methanamine was obtained.

$^1$H-NMR (δ, CDCl$_3$): 1.1-1.4 (m, 3H); 1.6-1.9 (m, 4H); 1.9-2.1 (m, 2H); 2.4-2.6 (m, 4H); 2.7-2.8 (m, 2H); 2.9-3.1 (m, 2H); 3.77 (s, 3H); 6.7-6.9 (m, 2H); 7.0-7.2 (m, 2H).

5b) N-({1-[2-(4-Methoxyphenyl)ethyl]piperidin-4-yl}methyl)-2-methyl-2H-indazole-3-carboxamide hydrochloride 1-[2-(4-Methoxyphenyl)ethyl]-4-piperidinylmethanamine (5a) (6.8 g; 0.027 mol) was added in small portions to a suspension of chloride of 2-methyl-2H-indazole-3-carboxylic acid (1b) (5.3 g; 0.027 mol) in toluene (200 ml). The mixture thus obtained was stirred for 48 h at room temperature and was then filtered. The solid compound was suspended in 1N NaOH and extracted 3 times with dichloromethane. The solvent was removed by evaporation at reduced pressure and the residue was crystallized first from isopropyl ether/isopropanol and then from ethyl acetate/absolute ethanol. The compound was then converted to its hydrochloride by dissolution in ethanol followed by treatment with 5N hydrochloric ethanol for 3 h at room temperature and then removal of the solvent by evaporation at reduced pressure.

After crystallization from ethyl acetate/absolute ethanol, 5.0 g of N-({1-[2-(4-methoxyphenyl)ethyl]piperidin-4-yl}methyl)-2-methyl-2H-indazole-3-carboxamide hydrochloride was obtained.

m.p.=80° C. (decomp.)

$^1$H-NMR (δ, DMSO-d6): 1.5-2.1 (m, 5H); 2.8-3.5 (m, 8H); 3.58 (d, J=12 Hz, 2H); 3.73 (s, 3H); 4.30 (s, 3H); 6.90 (d, J=9 Hz, 2H); 7.1-7.4 (m, 4H); 7.69 (d, J=9 Hz, 1H); 7.84 (d, J=9 Hz, 1H); 8.67 (t, J=6 Hz, 1H); 10.7-11.0 (s broad, 1H).

MS shows 407 (MH$^+$) base peak.

EXAMPLE 6

N3-2-Dimethyl-N3-[(1-{2-[4-(methyloxy)phenyl]ethyl}piperidin-4-yl)methyl]-2H-indazole-3-carboxamide hydrochloride hydrate (Compound No. 6)

(Compound I: R1=H, R2=CH$_3$, X=—C(O)N(R5)-, R3=4-CH$_3$—, R4=H, R5=CH$_3$, n=1, p=2, m=2, Y=CH, W=N, R6+R7=—CH$_2$—CH$_2$—)

6a) ({1-[2-(4-Methoxyphenyl)ethyl]-4-piperidinyl}methyl)formamide (Compound XII: R3=4-CH$_3$O, R4=H, R6+R7=—CH$_2$—CH$_2$—, n=1, p=m=2, R=H)

Formic acid (0.60 ml; 0.016 mol) was added dropwise, in a nitrogen atmosphere, at a temperature of 0° C., to a flask containing acetic anhydride (1.25 ml; 0.0112 mol). The mixture thus obtained was heated under reflux for 2 h and, after cooling to room temperature, a solution of 1-[2-(4-methoxyphenyl)ethyl]-4-piperidinylmethanamine (5a) (1.24 g; 502 mmol) in THF (10 ml) was added.

The mixture was reacted for 18 h. The suspension was then concentrated by evaporation at reduced pressure. 1.0 g of ({1-[2-(4-methoxyphenyl)ethyl]-4-piperidinyl}methyl)formamide was thus obtained.

GC/MS (m/z: 155 base peak; 121; 110).

6b) 1-{1-[2-(4-Methoxyphenyl)ethyl]-4-piperidinyl}-N-methylmethanamine (Compound II: R3=4-CH$_3$O, R4=H, R5=CH$_3$, R6+R7=—CH$_2$—CH$_2$—, n=1, p=2, m=2)

A solution of borane-dimethylsulphide 2N complex in n-hexane (6 ml) was added dropwise to a suspension of ({1-[2-(4-methoxyphenyl)ethyl]-4-piperidinyl}methyl)formamide (1.0 g; 0.0041 mol) (6a) in 20 ml of THF at 0° C. The mixture was heated under reflux for 5 h and was then cooled to 0° C. At this temperature, 2 ml of methanol was then added and the reaction mixture was stirred vigorously for 1 h.

Next, gaseous HCl was bubbled into the reaction mixture until acidity was complete. Then the mixture was refluxed for 1 h. After cooling it, methanol (10 ml) was added, and the solvent was evaporated at reduced pressure. The residue was taken up in water and washed 3 times with ethyl acetate. The aqueous phase was alkalized with 6N NaOH and extracted 3 times with dichloromethane. The organic phase was dried over $Na_2SO_4$, filtered and evaporated at reduced pressure. 0.6 g of 1-{1-[2-(4-methoxyphenyl)ethyl]-4-piperidinyl}-N-methylmethanamine was thus obtained.

GC/MS (m/z: 127; 110; 96).

6c) N3-2-Dimethyl-N3-[(1-{2-[4-(methyloxy)phenyl]ethyl}piperidin-4-yl)methyl]-2H-indazole-3-carboxamide hydrochloride hydrate 1-{1-[2-(4-Methoxyphenyl)ethyl]-4-piperidinyl}-N-methylmethanamine (prepared as described in the previous Example 6b) (1.4 g; 0.0052 mol) was added, in small portions, to a solution of chloride of 2-methyl-2H-indazole-3-carboxylic acid (1b) (1.1 g; 0.0061 mol) in toluene (20 ml). The mixture thus obtained was stirred for 18 h at room temperature and was then filtered.

The solid residue was taken up in 1N NaOH and extracted with dichloromethane. The combined organic phases were dried over $Na_2SO_4$ and the solvent was removed by evaporation at reduced pressure. The solid residue was converted to hydrochloride by dissolution in ethanol, addition of an excess of 5N hydrochloric ethanol, stirring for 3 h at room temperature and then removal of the solvent by evaporation at reduced pressure.

After crystallization from ethyl acetate/absolute ethanol, 0.8 g of N3-2-dimethyl-N3-[(1-{2-[4-(methyloxy)phenyl]ethyl}piperidin-4-yl)methyl]-2H-indazole-3-carboxamide hydrochloride hydrate was obtained.

m.p.=132.5-136.5° C.

Elemental analysis for C, 25; HT, 35; ClN, 4; O, 3

|  | C | H | N | Cl |
|---|---|---|---|---|
| Found % | 62.95 | 7.65 | 11.61 | 7.59 |
| Calculated % | 63.21 | 7.43 | 11.79 | 7.76 |

$^1$H-NMR (δ, DMSO-d6+$D_2O$): 1.5-2.3 (m, 5H); 2.7-3.7 (m, 13H); 3.11 (s, 3H); 3.73 (s, 3H); 4.15 (s, 3H); 6.90 (d, J=8 Hz, 2H); 7.1-7.3 (m, 3H); 7.33 (t, J=8 Hz, 1H); 7.59 (d, J=8 Hz, 1H); 7.69 (d, J=9 Hz, 1H).

EXAMPLE 7

N-({1-[2-(4-Fluorophenyl)ethyl]piperidin-4-yl}methyl)-2-(2-methoxyethyl)-2H-indazole-3-carboxamide hydrochloride (Compound No. 7)

(Compound I: R1=H, R2=$CH_2CH_2OCH_3$, X=—C(O)N(R5)-, R3=4-F, R4=H, R5=H, n=1, p=2, m=2, Y=CH, W=N, R6+R7=—$CH_2$—$CH_2$—)

7a) 2-(2-Methoxyethyl)-2H-indazole-3-ethyl carboxylate (Compound III: R1=H, R2=$CH_3OCH_2CH_2$, Z=$CH_3CH_2O$)

Potassium carbonate (33.6 g; 0.243 mol) and, dropwise, 2-bromoethyl methyl ether (46 ml; 0.49 mol) were added to a solution of ethyl ester of 1H(2H)-indazole-3-carboxylic acid (15.4 g; 0.0811 mol) in absolute ethanol (200 ml).

The reaction mixture was stirred for 48 h. The solvent was then removed by evaporation at reduced pressure. The residue was taken up in chloroform and washed with water 3 times.

The organic phase was dried over $Na_2SO_4$, and, after filtration and evaporation of the solvent, approx. 10 g of raw compound was obtained. This was purified by flash chromatography using an n-hexane/ethyl acetate 7:3 mixture as eluent. 4.5 g of 2-(2-methoxyethyl)-2H-indazole-3-ethyl carboxylate was thus obtained.

$^1$H-NMR (δ, $CDCl_3$): 1.50 (t, J=6 Hz, 3H); 3.33 (s, 3H); 3.91 (t, J=6 Hz, 2H); 4.49 (q, J=6 Hz, 2H); 5.13 (t, J=6 Hz, 2H); 7.2-7.4 (m, 2H); 7.79 (d, J=9 Hz,1H); 8.02 (d, J=9 Hz,1H).

7b) 2-(2-Methoxyethyl)-2H-indazole-3-carbonyl chloride (Compound III: R1=H, R2=$CH_3OCH_2CH_2$, Z=Cl)

The ester 2-(2-methoxyethyl)-2H-indazole-3-ethyl carboxylate (prepared as described in the previous Example 7a) (4.26 g; 0.0171 mol) was hydrolysed in an aqueous solution (30 ml) of sodium hydroxide (1.16 g; 0.0291 mol). The reaction mixture was heated under reflux for 2 h, cooled to room temperature and acidified with 6N HCl until there was complete precipitation of 2-(2-methoxyethyl)-2H-indazole-3-carboxylic acid which, after separation by filtration and stove-drying under vacuum, was in the form of a white solid (3.6 g), which was used without further purification in the next reaction.

Thienyl chloride (2.6 ml; 0.036 mol) was added to a suspension of 2-(2-methoxyethyl)-2H-indazole-3-carboxylic acid (3.6 g; 0.016 mol) in toluene (100 ml) and the reaction mixture was heated under reflux for 24 h. The solvent was removed by evaporation at reduced pressure and the residue was taken up twice in n-hexane. 3.9 g of 2-(2-methoxyethyl)-2H-indazole-3-carbonyl chloride was thus obtained.

$^1$H-NMR (δ, $CDCl_3$): 3.29 (s, 3H); 3.84 (t, J=6 Hz, 2H); 5.11 (t, J=6 Hz, 2H); 7.1-7.4 (m, 2H); 7.74 (d, J=9 Hz, 1H); 7.99 (d, J=9 Hz, 1H).

7c) 1-(2-Bromoethyl)-4-fluorobenzene (Compound V: R3=4-F, R4=H, m=2, Q=Br)

60.8 g of 47% hydrobromic acid (0.353 mol) was added slowly to a solution of 2-(4-fluorophenyl)ethanol (20 g; 0.143 mol) in concentrated sulphuric acid (8.5 ml; 0.16 mol). The mixture was heated under reflux for 3 h, then it was cooled to room temperature and 50 ml of dichloromethane was added.

The organic phase was separated and washed successively with 1N NaOH and water and was then dried over $Na_2SO_4$. After filtration and evaporation of the solvent at reduced pressure, approx. 13 g of raw compound was obtained, which was purified by flash chromatography (n-hexane/ethyl acetate=9/1). 10.6 g of 1-(2-bromoethyl)-4-fluorobenzene was thus obtained.

$^1$H-NMR (δ, $CDCl_3$): 3.13 (t, J=9 Hz, 2H); 3.54 (t, J=9 Hz, 2H); 6.9-7.3 (m, 4H)

7d) 1-[2-(4-Fluorophenyl)ethyl]-4-piperidine methanamine (Compound XI: R3=4-F, R4=H, R6+R7=—$CH_2$—$CH_2$—, n=1, p=2, m=2)

N-hexahydro-4-pyridinylmethyl-N-phenylmethylidenamine (17.9 g; 0.0879 mol) was dissolved in absolute ethanol (100 ml) containing anhydrous potassium carbonate (24.3 g; 0.176 mol) and 1-(2-bromoethyl)-4-fluorobenzene (prepared as described in the previous Example 7c) (18.0 g; 0.088 mol). The reaction mixture was heated under reflux for 24 h. After cooling to room temperature, the suspension was filtered and the solvent was evaporated at reduced pressure. The residue obtained was suspended in 3N HCl (120 ml) and stirred at room temperature for 3 h.

The acidic aqueous phase was washed 4 times with ethyl acetate, then it was alkalized to pH approx. 13 with 6N NaOH and, finally, it was extracted 3 times with ethyl acetate. The organic phase thus obtained was dried over anhydrous $Na_2SO_4$ and, after filtration, the solvent was removed by evaporation at reduced pressure to give 17.2 g of 1-[2-(4-fluorophenyl)ethyl]-4-piperidine methanamine.

$^1$H-NMR (δ, $CDCl_3$): 1.2-1.5 (m, 5H); 1.6-1.8 (m, 2H); 1.9-2.1 (m, 2H); 2.4-2.6 (m, 4H); 2.7-2.8 (m, 2H); 2.9-3.1 (m, 2H); 6.9-7.2 (m, 4H).

MS shows 237 (MH+), 220 (base peak).

7e) N-({1-[2-(4-Fluorophenyl)ethyl]piperidin-4-yl}methyl-2-(2-methoxyethyl)-2H-indazole-3-carboxamide hydrochloride 1-[2-(4-Fluorophenyl)ethyl]-4-piperidine methanamine (prepared as described in the previous Example 7d) (3.23 g; 0.0131 mol) and triethylamine (5.4 ml; 0.039 mol) were added to a solution of 2-(2-methoxyethyl)-2H-indazole-3-carbonyl chloride (prepared as described in the previous Example 7b) (3.26 g; 0.0131 mol) in toluene (50 ml).

The reaction mixture was stirred under reflux for 5 h and then the solvent was evaporated at reduced pressure. The residue was taken up in ethyl acetate and was washed successively with 0.1N NaOH and water. The organic phase was dried over anhydrous $Na_2SO_4$ and, after filtration, the solvent was removed by evaporation at reduced pressure. 4.7 g of raw compound was obtained, which was purified by flash chromatography ($CHCl_3/CH_3OH/NH_3$=98/2/0.2).

The compound obtained (1.5 g) was converted to the corresponding hydrochloride by dissolution in ethyl acetate, treatment with an excess of 5N hydrochloric ethanol at room temperature for 3 h, removal of the solvent by evaporation at reduced pressure and finally crystallization from absolute ethanol.

0.6 g of N-({1-[2-(4-fluorophenyl)ethyl]piperidin-4-yl}methyl)-2-(2-methoxyethyl)-2H-indazole-3-carboxamide hydrochloride was thus obtained.

m.p.=193.0-194.0° C.

Elemental analysis for C, 25; H, 31; N, 4; O, 2; F.HCl

|  | C | H | N | Cl |
|---|---|---|---|---|
| Found % | 63.21 | 6.79 | 11.69 | 7.50 |
| Calculated % | 63.20 | 6.79 | 11.80 | 7.46 |

$^1$H-NMR (δ, DMSO-d6): 1.5-2.0 (m, 5H), 2.8-3.7 (m, 10H); 3.19 (s, 3H); 3.80 (t, J=6 Hz, 2H); 4.88 (t, J=6 Hz, 2H); 7.1-7.4 (m, 6H); 7.70 (d, J=9 Hz, 1H); 7.82 (d, J=9 Hz, 1H); 8.6-8.8 (m, 1H); 10.7-11.0 (s broad, 1H).

EXAMPLE 8

N-({1-[2-(4-Fluorophenyl)ethyl]piperidin-4-yl}methyl)-2-methyl-2H-indazole-3-carboxamide hydrochloride (Compound No. 8)

(Compound I: R1=H, R2=$CH_3$, X=—C(O)N(R5)-, R3=4-F, R4=H, R5=H, n=1, p=2, m=2, Y=CH, W=N, R6+R7=—$CH_2$—$CH_2$—)

8a) N-({1-[2-(4-Fluorophenyl)ethyl]piperidin-4-yl}methyl)-2-methyl-2H-indazole-3-carboxamide hydrochloride The compound was obtained as described in Example 7e) using 4.0 g of chloride of 2-methyl-2H-indazole-3-carboxylic acid (prepared as described in the previous Example 1b) (0.021 mol), toluene (100 ml), 1-[2-(4-fluorophenyl)ethyl]-4-piperidine methanamine (7d) (4.8 g; 0.021 mol) and triethylamine (8.6 ml; 0.062 mol). 10.7 g of raw compound was obtained, which was purified by flash chromatography ($CHCl_3/CH_3OH/NH_3$=97/3/0.3).

The compound thus obtained (4.1 g) was converted to the corresponding hydrochloride by dissolution in ethanol, treatment with an excess of 5N hydrochloric ethanol at room temperature for 3 h, removal of the solvent by evaporation at reduced pressure and finally crystallization from absolute ethanol/ethyl acetate.

4.3 g of N-({1-[2-(4-fluorophenyl)ethyl]piperidin-4-yl}methyl)-2-methyl-2H-indazole-3-carboxamide hydrochloride was thus obtained.

m.p.=208.0-209.0° C.

Elemental analysis for C, 23; H, 27; N, 4; OF.HCl

|  | C | H | N | Cl |
|---|---|---|---|---|
| Found % | 64.00 | 6.54 | 12.89 | 8.34 |
| Calculated % | 64.10 | 6.55 | 13.00 | 8.23 |

$^1$H-NMR (δ, DMSO-d6): 1.6-2.0 (m, 5H); 2.8-3.7 (m, 10H); 4.32 (s, 3H); 7.1-7.4 (m, 6H); 7.69 (d, J=9 Hz, 1H); 7.85 (d, J=9 Hz, 1H); 8.6-8.8 (m, 1H); 10.9-11.1 (s broad, 1H).

EXAMPLE 9

2-(2,4-Difluorophenyl)-N-({1-[(2-methyl-2H-indazole-3-yl)carbonyl]piperidin-4-yl}methyl)ethanamine hydrochloride (Compound No. 9)

(Compound I: R1=H, R2=$CH_3$, X=—C(O)N(R5)-, R3=4-F, R4=2-F, R5+R6=—$CH_2$—$CH_2$—, n=2, p=1, m=2, Y=CH, W=N, R7=H)

9a) 1-{1-[(2-Methyl-2H-indazol-3-yl)carbonyl]piperidin-4-yl}methanamine (Compound XVI: R1=H, R2=CH3, R5+R6=—$CH_2$—$CH_2$—, n=2, p=1)

N-Hexahydro-4-pyridinylmethyl-N-phenylmethylidenamine (11.3 g; 0.0558 mol) and triethylamine (9.3 ml; 0.066 mol) were added to a solution of chloride of 2-methyl-2H-indazole-3-carboxylic acid (prepared as described in the previous Example 1b) (10.8 g; 0.0558 mol) in toluene (150 ml).

The mixture was heated under reflux for 5 h. Then it was cooled to room temperature and filtered. The solvent was evaporated at reduced pressure. The residue was stirred at room temperature with 3N HCl (80 ml) for 5 h. The acidic solution was washed 3 times with ethyl acetate. Then it was alkalized with 12N NaOH. The alkaline aqueous phase was extracted with dichloromethane 3 times.

The combined organic phases were dried over anhydrous $Na_2SO_4$. Then they were filtered and the solvent was evaporated at reduced pressure. Approximately 16 g of raw compound was thus obtained, and was purified by flash chromatography ($CHCl_3/CH_3OH/NH_3$=95/5/0.5). 13.4 g of 1-{1-[(2-methyl-2H-indazol-3-yl)carbonyl]piperidin-4-yl}methanamine was obtained.

GC/MS (m/z) shows 272, 159 (base peak).

9b) 2-[2,4-Difluorophenyl)ethyl methanesulphonate (Compound V: R3=2-F, R4=4-F, m=2, Q=$CH_3OSO_2$)

A solution of (2,4-difluorophenyl)acetic acid (15.0 g; 0.0871 mol) in ethyl ether (100 ml) was added slowly to a suspension of lithium aluminium hydride (6.58 g; 0.174 mol) in ethyl ether (100 ml). The mixture was heated under reflux for 5 h and then brought to room temperature. The excess hydride was removed by adding 1N HCl (150 ml). The acid phase was separated and then extracted 3 times with ethyl ether. The combined organic phases were washed twice with 1N NaOH, dried over $Na_2SO_4$ and, after filtration, the solvent was evaporated at reduced pressure. 6.4 g of the desired compound was thus obtained, and was used without further purification for subsequent reaction.

Methanesulphonyl chloride (3.3 ml; 0.043 mol) and triethylamine (5.9 ml; 0.043 mol) were added to a solution of 2-(2,4-difluorophenyl)ethanol (6.4 g; 0.0426 mol) in dichloromethane (100 ml). The solution was cooled for 1 h at 0° C. and then brought to room temperature for 1 h. The reaction mixture was then treated by washing, successively, with 5N sulphuric acid (20 ml), water (50 ml), a 5% solution of $NaHCO_3$ (50 ml) and water (50 ml). The organic phase was then dried over $Na_2SO_4$, filtered and concentrated at reduced pressure. The residue was taken up twice in $CCl_4$, thus obtaining 6.42 g of 2-(2,4-difluorophenyl)ethyl methanesulphonate.

$^1$H-NMR (δ, $CDCl_3$): 2.92 (s, 3H); 3.07 (t, J=6 Hz, 2H); 4.40 (t, J=6 Hz, 2H); 6.7-6.9 (m, 2H); 7.1-7.3 (m, 1H).

9c) 2-(2,4-Difluorophenyl)-N-({1-[(2-methyl-2H-indazole-3-yl)carbonyl]piperidin-4-yl}methyl)ethanamine hydrochloride $K_2CO_3$ (3.7 g; 0.027 mol) and 1-{1-[(2-methyl-2H-indazol-3-yl)carbonyl]piperidin-4-yl}methanamine (prepared as described in the previous Example 9a) (6.73 g; 0.0247 mol) were added to a solution of 2-(2,4-difluorophenyl)ethyl methanesulphonate (9b) (6.42 g; 0.0271 mol) in absolute ethanol (150 ml).

The mixture was heated under reflux for 30 h and then the solvent was evaporated at reduced pressure. The residue was taken up in ethyl acetate and washed 3 times with water. The organic phase was dried over $Na_2SO_4$, filtered and concentrated at reduced pressure. Approx. 15 g of raw compound was thus obtained, which was purified by flash chromatography ($CHCl_3/CH_3OH/NH_3$=99/1/0.1). The compound thus obtained (2.5 g) was converted to its hydrochloride by dissolving in absolute ethanol and treatment with an excess of 5N hydrochloric ethanol for 3 h. After evaporation of the solvent at reduced pressure, the solid residue was crystallized from ethanol/ethyl acetate, obtaining 0.7 g of 2-(2,4-difluorophenyl)-N-({1-[(2-methyl-2H-indazol-3-yl)carbonyl]piperidin-4-yl}methyl)ethanamine hydrochloride.

m.p.=108.0-110.0° C.

Elemental analysis for C, 23; H, 26; N, 4; OF, 2.HCl

|  | C | H | N | Cl |
|---|---|---|---|---|
| Found % | 61.68 | 5.97 | 12.46 | 8.00 |
| Calculated % | 61.53 | 6.06 | 12.48 | 7.90 |

$^1$H-NMR (δ, DMSO-d6): 1.0-2.2 (m, 5H); 2.8-3.3 (m, 8H); 3.4-4.9 (m, 2H); 4.17 (s, 3H); 7.0-7.5 (m, 5H); 7.62 (d, J=9 Hz, 1H); 7.69 (d, J=9 Hz, 1H); 9.1-9.5 (s broad, 2H).

EXAMPLE 10

2-(4-Fluorophenyl)-N-({1-[(2-methyl-2H-indazol-3-yl)carbonyl)piperidin-4-yl}methyl]ethanamine hydrochloride (Compound No. 10)

(Compound I: R1=H, R2=$CH_3$, X=—C(O)N(R5)-, R3=4-F, R4=H, R5+R6=—$CH_2$—$CH_2$—, n=2, p=1, m=2, Y=CH, W=N, R7=H)

10a) 2-(4-Fluorophenyl)-N({1-[2-methyl-2H-indazol-3-yl)carbonyl]piperidin-4-yl}methyl)ethanamine hydrochloride The desired compound was obtained as described in Example 9c) using 4.10 g of 1-(2-bromoethyl)-4-fluorobenzene (prepared as described in the previous Example 7c) (0.0201 mol), 5.0 g of 1-{1-[(2-methyl-2H-indazol-3-yl)carbonyl]piperidin-4-yl}methanamine (prepared as described in the previous Example 9a) (0.018 mol), 2.77 g of $K_2CO_3$ (0.0201 mol) and 100 ml of absolute ethanol.

Approximately 7 g of raw compound was thus obtained, and was purified by flash chromatography ($CHCl_3/CH_3OH/NH_3$=98/2/0.2). The compound obtained (3.5 g) was converted to its hydrochloride by dissolving in absolute ethanol and treatment with excess of 5N hydrochloric ethanol for 3 h. After evaporation of the solvent at reduced pressure, the solid residue is crystallized from ethanol/diisopropyl ether, obtaining 2.5 g of 2-(4-fluorophenyl)-N-({1-[(2-methyl-2H-indazol-3-yl)carbonyl]piperidin-4-yl}methyl)ethanamine hydrochloride.

m.p.=198-199° C.

Elemental analysis for C, 23; H, 27; N, 4; OF.HCl

|  | C | H | N | Cl |
|---|---|---|---|---|
| Found % | 64.14 | 6.54 | 13.00 | 8.24 |
| Calculated % | 64.10 | 6.55 | 13.00 | 8.23 |

$^1$H-NMR (δ, DMSO-d6): 1.1-2.2 (m, 5H); 2.7-3.3 (m, 8H); 3.4-4.9 (m, 2H); 4.17 (s, 3H); 7.1-7.4 (m, 6H); 7.61 (d, J=9 Hz, 1H); 7.68 (d, J=9 Hz, 1H); 9.0-9.4 (s broad, 2H).

EXAMPLE 11

N-Ethyl-2-(4-fluorophenyl)-N-({1-[(2-methyl-2H-indazol-3-yl)carbonyl]piperidin-4-yl}methyl)ethanamine hydrochloride (Compound No. 11)

(Compound I: R1=H, R2=CH$_3$, X=—C(O)N(R5)-, R3=4-F, R4=H, R5+R6=—CH$_2$—CH$_2$—, n=2, p=1, m=2, Y=CH, W=N, R7=CH$_3$CH$_2$)

11a) N-Ethyl-2-(4-fluorophenyl)-N-({1-[(2-methyl-2H-indazol-3-yl)carbonyl]piperidin-4-yl}methyl)ethanamine hydrochloride K$_2$CO$_3$ (0.71 g; 0.0052 mol), potassium iodide (10 mg; 0.062 mmol) and ethyl bromide (0.54 ml; 0.0072 mol) were added to a solution of 2-(4-fluorophenyl)-N-({1-[(2-methyl-2H-indazol-3-yl)carbonyl]piperidin-4-yl}methyl)ethanamine (10a) (1.7 g; 0.0043 mol) in absolute ethanol (20 ml). The mixture was heated under reflux for 48 h and then the solvent was evaporated at reduced pressure. The residue was taken up in chloroform and was washed with water twice. The organic phase was dried over Na$_2$SO$_4$, filtered and concentrated at reduced pressure. The resultant raw compound (1.5 g) was purified by flash chromatography (ethyl acetate/n-hexane/ammonia=96/4/0.2). The compound obtained (0.5 g) was converted to its hydrochloride by dissolving in absolute ethanol and treatment with an excess of 5N hydrochloric ethanol for 3 h. After evaporation of the solvent at reduced pressure, the solid residue was crystallized from ethanol/ethyl acetate, obtaining 0.15 g of N-ethyl-2-(4-fluorophenyl)-N-({1-[(2-methyl-2H-indazol-3-yl)carbonyl]piperidin-4-yl}methyl)ethanamine hydrochloride.

$^1$H-NMR (δ, CDCl$_3$): 0.6-2.4 (m, 5H); 1.44 (t, J=9 Hz, 3H); 2.7-3.7 (m, 12H); 4.28 (s, 3H); 6.9-7.4 (m, 6H); 7.46 (d, J=9 Hz, 1H); 7.72 (d, J=9 Hz, 1H); 12.0-12.7 (s broad, 2H).

MS shows 423 (MH$^+$), 159 (base peak).

EXAMPLE 12

N-({1-[2-(2-fluorophenyl)ethyl)piperidin-4-yl}methyl)-2-methyl-2H-indazole-3-carboxamide (Compound No. 12)

(Compound I: R1=H, R2=CH$_3$, X=—C(O)N(R5)-, R3=2-F, R4=H, R5=H, R6 +R7=—CH$_2$—CH$_2$—, n=1, p=2, m=2, Y=CH, W=N)

12a) {1-[2-(2-fluorophenyl)ethyl]-4-piperidine)methanamine (Compound XI: R3=2-F, R4=H, R6+R7=—CH$_2$—CH$_2$—, Y=CH, W=N, n=1, p=2, m=2)

{1-[2-(2-Fluorophenyl)ethyl]-4-piperidine}methanamine was prepared according to the procedure described in Example 7d) using as reactants N-hexahydro-4-pyridinylmethyl-N-phenylmethylidenamine (2.03 g; 10 mmol), and 1-(2-bromoethyl)-2-fluorobenzene (2.04 g; 10 mmol).

1.42 g of 1-[2-(2-fluorophenyl)ethyl]-4-piperidine methanamine was obtained.

$^1$H-NMR (δ, CDCl$_3$): 1.0-1.4 (m, 2H), 1.5-2.1 (m, 5H), 2.4-3.0 (m, 10H), 6.8-7.2 (m, 4H).

12b) N-({1-[2-(2-fluorophenyl)ethyl]piperidin-4-yl)methyl)-2-methyl-2H-indazole-3-carboxamide The compound was obtained according to the procedure described in Example 7e) using as reactants 2-methyl-2H-indazole-3-carbonyl chloride (Example 1b) (880 mg; 4.5 mmol) and 1-[2-(2-fluorophenyl)ethyl]-4-piperidine methanamine (Example 12a) (1.06 g; 4.5 mmol).

350 mg of N-({1-[2-(2-fluorophenyl)ethyl]piperidin4-yl}methyl)-2-(2-methoxyethyl)-2H-indazole-3-carboxamide was thus obtained.

m.p.=128-130° C.

Elemental analysis for C, 23; H, 27; N, 4; OF

|  | C | H | N |
|---|---|---|---|
| Found % | 70.21 | 6.79 | 14.39 |
| Calculated % | 70.03 | 6.90 | 14.20 |

$^1$H-NMR (DMSO-d$_6$, δ ppm): 1.15-1.35 (m, 2 H) 1.50-1.83 (m, 3 H) 1.97 (t, J=10.82 Hz, 2 H) 2.42-2.57 (m, 2 H) 2.77 (t, J=7.60 Hz, 2 H) 2.94 (d, J=10.82 Hz, 2 H) 3.25 (t, J=6.28 Hz, 2 H) 4.28 (s, 3 H) 7.06-7.38 (m, 6 H) 7.67 (d, J=8.77 Hz, 1 H) 7.77 (d, J=8.18 Hz, 1 H) 8.54 (t, J=5.70 Hz, 1 H).

EXAMPLE 13

2-ethyl-N-({1-[2-(4-fluorophenyl)ethyl]piperidin-4-yl}methyl)-2 H-indazole-3-carboxamide hydrochloride (Compound No. 13)

(Compound I: R1=H, R2=CH$_2$CH$_3$, X=—C(O)N(R5)-, R3=4-F, R4=H, R5=H, R6 +R7=—CH$_2$—CH$_2$—, n=1, p=2, m=2, Y=CH, W=N)

13a) methyl ester of 2-ethyl-2H-indazole-3-carboxylic acid (Compound X; R1=H, R2=CH$_2$CH$_3$)

The compound was obtained according to the procedure described in Example 1a) using as reactants the methyl ester of 1H(2H)-indazole-3-carboxylic acid (7.4 g; 49.9 mmol) and ethyl bromide (3.73 ml; 50 mmol).

4.5 g of methyl ester of 2-ethyl-2H-indazole-3-carboxylic acid was obtained.

$^1$H-NMR (δ, DMSO-d$_6$): 1.55 (t, J=7.3 Hz, 3 H), 4.09 (s, 3 H), 4.62 (q, J=7.3 Hz, 2 H), 7.2-7.4 (m, 1 H), 7.5-7.6 (m, 1), 7.7-7.8 (m, 1), 7.9-8.1 (m, 1H).

13b) 2-ethyl-2H-indazole-3-carbonyl chloride (Compound III: R1=H, R2=CH$_2$CH$_3$, Z=Cl)

The compound was obtained according to the procedure described in Example 1b) using as reactant the methyl ester of 2-ethyl-2H-indazole-3-carboxylic acid (Example 13a) (4.0 g; 19.6 mmol).

3.5 g of 2-ethyl-2H-indazole-3-carbonyl chloride was thus obtained.

hu 1H-NMR (δ, DMSO-d$_6$): 1.51 (t, J=7.3 Hz, 3 H), 4.59 (q, J=7.3 Hz, 2 H), 7.3-7.4 (m, 1H), 7.5-7.6 (m, 1), 7.7-7.8 (m, 1), 7.9-8.1 (m, 1H),

13c) N-({1-[2-(4-fluorophenyl)ethyl]piperidin-4-yl-methyl)-2-ethyl-2H-indazole-3-carboxamide hydrochloride The compound was obtained as described in Example 7e) using 2-ethyl-2H-indazole-3-carbonyl chloride (Example 13b) (1.05 g; 5.4 mmol) and 1-[2-(4-fluorophenyl)ethyl]-4-piperidine methanamine (Example 7d) (1.1 g; 5.4 mmol).

190 mg of N-({1-[2-(4-fluorophenyl)ethyl]piperidin-4-yl}methyl)-2-ethyl-2H-indazole-3-carboxamide hydrochloride was obtained.

m.p.=182-186° C.

Elemental analysis for C, 24; H, 29; N, 4; OF.HCl

|  | C | H | N | Cl |
|---|---|---|---|---|
| Found % | 64.60 | 6.54 | 12.69 | 8.04 |
| Calculated % | 64.78 | 6.80 | 12.59 | 7.97 |

$^1$H-NMR (DMSO-$d_6$, δ ppm): 1.46 (t, J=7.27 Hz, 3 H) 1.51-1.75 (m, 2 H) 1.91 (br. s., 3 H) 2.66-3.84 (m, 10 H) 4.68 (q, J=7.27 Hz, 2 H) 7.08-7.39 (m, 6 H) 7.70 (d, J=8.59 Hz, 1 H) 7.80 (d, J=8.26 Hz, 1 H) 8.65 (t, J=5.28 Hz, 1 H) 10.30 (br. s., 1 H).

EXAMPLE 14

N-{1-[2-(4-fluorophenyl)ethyl]piperidin-4-yl}-2-methyl-2H-indazole-3-carboxamide hydrochloride (Compound No. 14)

(Compound I: R=H, R2=CH$_3$, X=—C(O)N(R5)-, R3=4-F, R4=H, R5=H, R6 +R7=—CH$_2$—CH$_2$—, n=0, p=2, m=2, Y=CH, W=N)

14a) 1-[2-(4-fluorophenyl)ethyl]piperidine-4-amine (Compound XI: R3=4-F, R4=H, R6+R7=—CH$_2$—CH$_2$—, Y=CH, W=N, n=0, p=2, m=2)

Benzaldehyde (21.2 g; 0.2 mol) was added, dropwise, to a solution of 4-aminopiperidine (20 g; 0.2 mol) in toluene (80 ml). The solution thus obtained was stirred at room temperature. After 3 h the solvent was removed by evaporation at reduced pressure and the residue was taken up twice with toluene. 31 g N-(phenylmethylene)piperidine-4-amine was thus obtained, and was used in the subsequent reactions without further purification.

An aliquot of this product (1.88 g, 10 mmol) was used, according to the procedure described in Example 7d), together with 1-(2-bromoethyl)-4-fluorobenzene (Example 7c) (2.03 g; 10 mol).

1.3 g of 1-[2-(4-fluorophenyl)ethyl]piperidine-4-amine was thus obtained, and was used for the next reaction without further purification.

14b) N-{1-[2-(4-fluorophenyl)ethyl]piperidin-4-yl}-2-methyl-2H-indazole-3-carboxamide hydrochloride The compound was obtained as described in Example 7e) using as reactants 2-methyl-2H-indazole-3-carbonyl chloride (Example 1b) (1.15 g; 5.8 mmol) and 1-[2-(4-fluorophenyl)ethyl]piperidine-4-amine (Example 14a) (1.1 g; 5.8 mmol).

305 mg of N-{1-[2-(4-fluorophenyl)ethyl]piperidin-4-yl}-2-methyl-2H-indazole-3-carboxamide hydrochloride was thus obtained.

m.p.=224-228° C.

Elemental analysis for C, 22; H, 25; N, 4; OF.HCl

|  | C | H | N | Cl |
|---|---|---|---|---|
| Found % | 63.20 | 6.44 | 13.29 | 8.54 |
| Calculated % | 63.38 | 6.29 | 13.44 | 8.50 |

$^1$H-NMR (DMSO-$d_6$, δ ppm): 2.09 (br. s., 4 H) 2.72-3.83 (m, 8 H) 4.09 (br. s., 1 H) 4.29 (s, 3 H) 7.08-7.26 (m, 3 H) 7.32 (t, J=7.10 Hz, 3 H) 7.68 (d, J=8.59 Hz, 1 H) 7.75 (d, J=8.26 Hz, 1 H) 8.78 (br. s., 1 H) 10.63 (br. s., 1 H).

EXAMPLE 15

N-{1-[2-(4-fluorophenyl)ethyl]pyrrolidin-3-yl}-2-methyl-2H-indazole-3-carboxamide (Compound No. 15)

(Compound I: R1=H, R2=CH$_3$, X=—C(O)N(R5)-, R3=4-F, R4=H, R5=H, R6+R7=—CH$_2$—CH$_2$—, n=0, p=1, m=2, Y=CH, W=N)

15a) 1-[2-(4-fluorophenyl)ethyl]pyrrolidine-3-amine (Compound XI: R3=4-F, R4=H, R6+R7=—CH$_2$—CH$_2$—, Y=CH, W=N, n=0, p=1, m=2)

Benzaldehyde (21.2 g; 0.20 mol) was added, dropwise, to a solution of 3-aminopyrrolidine (17.2 g; 0.20 mol) in toluene (80 ml). The solution thus obtained was stirred at room temperature. After 3 h the solvent was removed by evaporation at reduced pressure and the residue was taken up twice with toluene. 21 g N-(phenylmethylene)pyrrolidine-3-amine was thus obtained, and was used in subsequent reactions without further purification.

An aliquot of this product (1.7 g, 10 mmol) was used, according to the procedure described in Example 7d), together with 1-(2-bromoethyl)-4-fluorobenzene (Example 7c) (2.0 g; 10 mmol).

1.4 g of 1-[2-(4-fluorophenyl)ethyl]pyrrolidine-3-amine was thus obtained, and was used in the next reaction without further purification.

15b) N-{1-[2-(4-fluorophenyl)ethyl]pyrrolidin-3-yl}-2-methyl-2H-indazole-3-carboxamide The compound was obtained as described in Example 7e) using as reactants 2-methyl-2H-indazole-3-carbonyl chloride (Example 1b) (1.3 g; 6.7 mmol) and 1-[2-(4-fluorophenyl)ethyl]pyrrolidine-3-amine (Example 15a) (1.4 g; 6.7 mmol).

235 mg of N-{1-[2-(4-fluorophenyl)ethyl]pyrrolidin-3-yl}-2-methyl-2H-indazole-3-carboxamide was thus obtained.

m.p.=117-119° C.

Elemental analysis for C, 21; H, 23; N, 4; OF

|  | C | H | N |
|---|---|---|---|
| Found % | 69.01 | 6.44 | 15.29 |
| Calculated % | 68.83 | 6.33 | 15.29 |

$^1$H-NMR (DMSO-$d_6$, δ ppm): 1.83 (dddd, J=13.01, 7.67, 5.70, 5.48 Hz, 1 H) 2.11-2.26 (m, 1 H) 2.53-2.82 (m, 7 H) 2.92 (dd, J=9.35, 7.31 Hz, 1 H) 4.27 (s, 3 H) 4.39-4.53 (m, 1 H) 7.03-7.13 (m, 2 H) 7.19 (ddd, J=8.33, 6.58, 0.88 Hz, 1 H)

7.25-7.35 (m, 3 H) 7.66 (ddd, J=8.50, 1.00, 0.80 Hz, 1 H) 7.71 (ddd, J=8.33, 1.17, 1.02 Hz, 1 H) 8.64 (d, J=7.02 Hz, 1 H).

EXAMPLE 16

N-{1-[2-(4-fluorophenyl)ethyl]piperidin-3-yl}-2-methyl-2H-indazole-3-carboxamide (Compound No. 16)

(Compound I: R1=H, R2=$CH_3$, X=—C(O)N(R5)-, R3=4-F, R4=H, R5=H, R6+R7=—$CH_2$—$CH_2$—$CH_2$—, n=0, p=1, m=2, Y=CH, W=N)

16a) 1-[2-(4-fluorophenyl)ethyl]piperidine-3-amine (Compound XI: R3=4-F, R4=H, R6+R7=—$CH_2$—$CH_2$—$CH_2$—, Y=CH, W=N, n=0, p=1, m=2)

Benzaldehyde (21.2 g; 0.2 mol) was added, dropwise, to a solution of 3-aminopiperidine (20 g; 0.2 mol) in toluene (80 ml). The solution thus obtained was stirred at room temperature, After 3 h the solvent was removed by evaporation at reduced pressure and the residue was taken up twice with toluene. 29 g N-(phenylmethylene)piperidine-3-amine was thus obtained, and was used in the subsequent reactions without further purification.

An aliquot of this product (1.88 g, 10 mmol) was used, according to the procedure described in Example 7d), together with 1-(2-bromoethyl)-4-fluorobenzene (Example 7c) (2.0 g; 10 mmol).

1.5 g of 1-[2-(4-fluorophenyl)ethyl]piperidine-3-amine was thus obtained.

$^1$H-NMR (δ ppm, $CDCl_3$): 1.00-2.20 (m, 8 H), 2.40-2.90 (m, 7 H), 6.80-7.20 (m, 4 H)

16b) N-{1-[2-(4-fluorophenyl)ethyl]pyrrolidin-3-yl}-2-methyl-2H-indazole-3-carboxamide The compound was obtained as described in Example 7e) using as reactants 2-methyl-2H-indazole-3-carbonyl chloride (Example 1b) (1.13 g; 5.8 mmol) and 1-[2-{4-fluorophenyl)ethyl]piperidine-3-amine (Example 16a) (1.3 g; 5.8 mmol).

335 mg of N-{1-[2-(4-fluorophenyl)ethyl]pyrrolidin-3-yl}-2-methyl-2H-indazole-3-carboxamide was thus obtained.

m.p.=194-197° C.

Elemental analysis for C, 22; H, 25; N, 4; OF

|  | C | H | N |
|---|---|---|---|
| Found % | 69.31 | 6.64 | 14.79 |
| Calculated % | 69.45 | 6.62 | 14.73 |

$^1$H-NMR (DMSO-$d_6$, δ ppm): 1.38-1.64 (m, 2 H) 1.66-1.92 (m, 2 H) 2.05-2.26 (m, 2 H) 2.53-2.62 (m, 2 H) 2.67-2.82 (m, 3 H) 2.95 (d, J=8.18 Hz, 1 H) 3.94-4.13 (m, 1 H) 4.28 (s, 3 H) 7.00-7.11 (m, 2 H) 7.15-7.38 (m, 4 H) 7.67 (d, J=8.48 Hz, 1 H) 7.72 (d, J=8.18 Hz, 1 H) 8.30 (d, J=8.30 Hz, 1 H).

EXAMPLE 17

2-methyl-N-[(1-{2-[4-(trifluoromethyl)phenyl]ethyl}piperidin-4-yl)methyl]-2H-indazole-3-carboxamide (Compound No. 17)

(Compound I: R1=H, R2=$CH_3$, X=—C(O)N(R5)-, R3=4-$CF_3$, R4=H, R5=H, R6+R7=—$CH_2$—$CH_2$—, n=1, p=2, m=2, Y=CH, W=N)

17a) 1-(1-{2-[4-(trifluoromethyl)phenyl]ethyl}piperidin-4-yl)methanamine (Compound XI: R3=4-$CF_3$, R4=H, R6+R7=—$CH_2$—$CH_2$—, Y=CH, W=N, n=1, p=2, m=2)

1-(1-{2-[4-(trifluoromethyl)phenyl]ethyl}piperidin-4-yl)methanamine was prepared according to the procedure described in Example 7d) using as reactants N-hexahydro-4-pyridinylmethyl-N-phenylmethylidene-amine (2.36 g; 10 mmol), and 1-(2-bromoethyl)-4-(trifluoromethyl)benzene (2.5 g; 10 mmol).

1.8 g of 1-(1-{2-[4-(trifluoromethyl)phenyl]ethyl}piperidin-4-yl)methanamine was obtained, and was used for the next reaction without further purification,

17b) 2-methyl-N-[(1-{2-[4-(trifluoromethyl)phenyl]ethyl}piperidin-4-yl)methyl]-2H-indazole-3-carboxamide The compound was obtained according to the procedure described in Example 7e) using as reactants 2-methyl-2H-indazole-3-carbonyl chloride (Example 1b) (1.28 g; 6.6 mmol) and 1-(1-{2-[4-(trifluoromethyl)phenyl]ethyl}piperidin-4-yl)methanamine (Example 17a) (1.8 g; 6.6 mmol).

415 mg of 2-methyl-N-[(1-{2-[4-(trifluoromethyl)phenyl]ethyl}piperidin-4-yl)methyl]-2H-indazole-3-carboxamide was thus obtained.

m.p.=174-176° C.

Elemental analysis for C, 24; H, 27; N, 4; OF, 3

|  | C | H | N |
|---|---|---|---|
| Found % | 64.71 | 6.29 | 12.59 |
| Calculated % | 64.85 | 6.12 | 12.60 |

$^1$H-NMR (DMSO-$d_6$, δ ppm): 1.14-1.34 (m, 2 H) 1.52-1.81 (m, 3 H) 1.97 (t, J=10.82 Hz, 2 H) 2.54 (t, J=8.00 Hz, 2 H) 2.83 (t, J=7.45 Hz, 2 H) 2.95 (d, J=11.11 Hz, 2 H) 3.25 (t, J=6.14 Hz, 2 H) 4.29 (s, 3 H) 7.16-7.25 (m, 1 H) 7.27-7.35 (m, 1 H) 7.46 (d, J=8.18 Hz, 2 H) 7.62 (d, J=8.18 Hz, 2 H) 7.67 (d, J=8.77 Hz: 1 H) 7.77 (d, J=8.48 Hz, 1 H) 8.54 (t, J=5.70 Hz, 1 H).

EXAMPLE 18

N-{1-[2-(2-fluorophenyl)ethyl)piperidin-4-yl}-2-methyl-2H-indazole-3-carboxamide (Compound No. 18)

(Compound I: R1=H, R2=CH$_3$, X=—C(O)N(R5)-, R3=2-F, R4=H, R5=H, R6 +R7=—CH$_2$—CH$_2$—, n=0, p=2, m=2, Y=CH, W=N)

18a) 1-[2-(2-fluorophenyl)ethyl]piperidine-4-amine (Compound XI: R3=2-F, R4=H, R6+R7=—CH$_2$—CH$_2$—, Y=CH, W=N, n=0, p=2, m=2)

The product was prepared using the procedure described in Example 7d) using as reactants N-(phenylmethylene)piperidine-4-amine (Example 14a) (1.8 g; 10 mmol) and 1-(2-bromoethyl)-2-fluorobenzene (2.5 g; 10 mmol).

1.3 g of 1-[2-(2-fluorophenyl)ethyl]piperidine-4-amine was thus obtained, and was used for the next reaction without further purification.

18b) N-{1-[2-(2-fluorophenyl)ethyl]piperidin-4-yl}-2-methyl-2H-indazole-3-carboxamide The compound was obtained according to the procedure described in Example 7e) using as reactants 2-methyl-2H-indazole-3-carbonyl chloride (Example 1b) (1.14 g; 5.8 mmol) and 1-[2-(2-fluorophenyl)ethyl]piperidine-4-amine (Example 18a) (1.3 g; 5.8 mmol).

188 mg of N-{1-[2-(2-fluorophenyl)ethyl]piperidin-4-yl}-2-methyl-2H-indazole-3-carboxamide was thus obtained.
m.p.=164-166° C.
Elemental analysis for C, 22; H, 25; N, 4; OF

|  | C | H | N |
|---|---|---|---|
| Found % | 69.61 | 6.59 | 14.59 |
| Calculated % | 69.45 | 6.62 | 14.73 |

$^1$H-NMR (DMSO-d$_6$, δ ppm): 1.64 (qd, J=11.55, 3.07 Hz, 2 H) 1.89 (d, J=11.98 Hz, 2 H) 2.13 (t, J=10.96 Hz, 2 H) 2.54 (t, J=8.48 Hz, 2 H) 2.79 (t, J=7.60 Hz, 2 H) 2.95 (d, J=11.69 Hz, 2 H) 3.73-3.98 (m, 1 H) 4.27 (s, 3 H) 7.07-7.39 (m, 6 H) 7.66 (dt, J=8.70, 0.91 Hz, 1 H) 7.73 (dt, J=8.40, 0.91 Hz, 1 H) 8.48 (d, J=7.70 Hz, 1 H).

EXAMPLE 19

N-{2-[4-(4-fluorophenyl)piperidin-1-yl]ethyl)-2-methyl-2H-indazole-3-carboxamide (Compound No.19)

(Compound I: R1=H, R2=CH$_3$, X=—C(O)N(R5)-, R3=4-F, R4=H, R5=H, R6 +R7=—CH$_2$—CH$_2$—, n=2, p=2, m=0, Y=N, W=CH)

19a) N-(2-aminoethyl)4-(4-fluorophenyl)piperidine (Compound II: R5=H, R6 +R7=—CH$_2$—CH$_2$—, R3=4-F, R4=H, Y=N, W=CH, n=2, p=2, m=0)

K$_2$CO$_3$ (1.61 g, 11.7 mmol) was added in small portions to a solution containing 4-(4-fluorophenyl)piperidine (1.05 g, 5.85 mmol) in anhydrous acetone (25 ml). Then a solution of (2-bromoethyl)phthalimide (164 g, 6.44 mmol) in anhydrous acetone (25 ml) was added slowly to the mixture while it was stirred at room temperature. At the end of addition (30 min) the mixture was heated to the reflux temperature for 24 h.

At the end of reaction, the mixture was cooled and filtered. The residual solution was then diluted with ethyl acetate (50 ml) and extracted with 1.5N HCl (3×20 ml). The combined acid phases were washed with ethyl acetate (2×10 ml) then strongly alkalized with 3N NaOH and extracted with dichloromethane (5×20 ml). The combined organic phases were dried over anhydrous Na$_2$SO$_4$ and evaporated at reduced pressure.

The residue obtained (607 mg) was then dissolved in methanol (11 ml) and treated with hydrazine monohydrate (2 ml, 41 mmol) at 90° C. for 2 h. The reaction mixture was cooled to room temperature, diluted with dichloromethane (50 ml) and extracted several times with 3N NaOH (5×15 ml). The organic phase was then rendered anhydrous with Na$_2$SO$_4$ and evaporated at reduced pressure.

400 mg of N-(2-aminoethyl)-4-(4-fluorophenyl)piperidine was thus obtained, and was used for the next reaction without further purification.

19b) N-{2-[4-(4-fluorophenyl)piperidin-1-yl]ethyl}-2-methyl-2H-indazole-3-carboxamide The compound was obtained according to the procedure described in Example 7e) using as reactants 2-methyl-2H-indazole-3-carbonyl chloride (Example 1b) (240 mg; 1.22 mol) and N-(2-aminoethyl)-4-(4-fluorophenyl)piperidine (Example 19a) (400 mg).

190 mg of N-{2-[4-(4-fluorophenyl)piperidin-1-yl]ethyl}-2-methyl-2H-indazole-3-carboxamide was thus obtained.
m.p.=105-107° C.
Elemental analysis for C, 22; H, 25; FN, 4; O

|  | C | H | N |
|---|---|---|---|
| Found % | 69.21 | 6.62 | 14.99 |
| Calculated % | 69.45 | 6.62 | 14.73 |

$^1$H NMR (DMSO-d$_6$ δ ppm): 1.55-1.83 (m, 4 H) 2.05-2.19, (m, 2 H) 2.53-2.56 (m, 0 H) 2.59 (t, J=6.58 Hz, 2 H) 3.06 (d, J=11.40 Hz, 2 H) 3.42-3.58 (m, 2 H) 4.31 (s, 3 H) 7.11 (t, J=8.92 Hz, 2 H) 7.17-7.37 (m, 5 H) 7.68 (d, J=8.48 Hz, 1 H) 7.92 (d, J=8.48 Hz, 1 H) 8.37 (t, J=5.41 Hz, 1 H)

EXAMPLE 20

N-{3-[4-(4-fluorophenyl)piperidin-1-yl]propyl}-2-methyl-2H-indazole-3-carboxamide (Compound No. 20)

(Compound I: R1=H, R2=CH$_3$, X=—C(O)N(R5)-, R3=4-F, R4=H, R5=H, R6+R7=—CH$_2$—CH$_2$—, n=3, p=2, m=0, Y=N, W=CH)

20a)
N-(3-aminopropyl)-4-(4-fluorophenyl)piperidine (Compound II: R5=H, R6+R7=—CH$_2$—CH$_2$—, R3=4-F, R4=H, Y=N, W=CH, n=3, p=2, m=0)

The compound was obtained according to the procedure described in Example 19a) using as reactants 4-(4-fluorophenyl)piperidine (1.10 g; 6.14 mol) and N-(3-bromopropyl) phthalimide (1.82 g, 6.78 mmol).

1.6 g of N-(3-aminopropyl)-4-(4-fluorophenyl)piperidine was thus obtained, and was used for the next reaction without further purification.

20b) N-{3-[4-(4-fluorophenyl)piperidin-1-yl]propyl}-2-methyl-2H-indazole-3-carboxamide The compound was obtained according to the procedure described in Example 7e) using as reactants 2-methyl-2H-indazole-3-carbonyl chloride (Example 1b) (236 mg; 1.21 mol) and N-(3-aminopropyl)-4-(4-fluorophenyl)piperidine (Example 20a) (550 mg).

120 mg of N-{3-[4-(4-fluorophenyl)piperidin-1-yl]propyl}-2-methyl-2H-indazole-3-carboxamide was thus obtained.

m.p.=136-140° C.
Elemental analysis for C, 23; H, 27; FN, 4; O

|  | C | H | N |
|---|---|---|---|
| Found % | 69.91 | 6.72 | 14.29 |
| Calculated % | 70.03 | 6.90 | 14.20 |

$^1$H NMR (CDCl$_3$, δ ppm): 1.26 (dq, J=12.9, 3.6 Hz, 2 H) 1.57 (bd, J=12.9 Hz, m, 2 H) 1.84 (q, J=5.7 Hz, 2 H) 1.94 (dt, J=11.7, 1.5 Hz, 2 H) 2.31 (tt, J=12.9, 4.4 Hz, 1 H) 2.58 (t, J=5.7 Hz, 2H) 3.39 (bd, J=11.7 Hz, 2 H) 3.70 (q, J=5.4 Hz, 2 H) 4.46 (s, 3 H) 6.58 (dd, J=8.4, 5.4 Hz, 2 H) 6.2 (t, J=8.7 Hz, 2H), 7.15-7.25 (m, 1 H) 7.3-7.4 (m, 1H), 7.81 (t, J=8.7 Hz, 2 H) 8.4 (bs, 1 H).

EXAMPLE 21

N-(1-benzylpiperidin-4-yl)-2-methyl-2H-indazole-3-carboxamide (Compound No. 21)

(Compound I: R1=H, R2=CH$_3$, X=—C(O)N(R5)-, R3=H, R4=H, R5=H, R6+R7=—CH$_2$—CH$_2$—, n=0, p=2, m=1, Y=CH, W=N)

21a) 1-benzylpiperidine-4-amine (Compound XI; R3=H, R4=H, R6+R7=—CH$_2$—CH$_2$—, Y=CH, W=N, n=0, p=2, m=1)

The product was prepared using the procedure described in Example 7d) using as reactants N-[phenylmethylene]piperidine-4-amine (Example 14a) (1.88 g; 10 mmol) and benzyl bromide (1.7 g; 10 mol).

1.7 g of 1-benzylpiperidine-4-amine was thus obtained, and was used for the next reaction without further purification.

21b) N-(1-benzylpiperidin-4-yl)-2-methyl-2H-indazole-3-carboxamide

The compound was obtained according to the procedure described in Example 7e) using as reactants 2-methyl-2H-indazole-3-carbonyl chloride (Example 1b) (1.74 g; 8.9 mmol) and 1-benzylpiperidine-4-amine (Example 21a) (1.7 g; 8.9 mmol).

460 mg of N-(1-benzylpiperidin-4-yl)-2-methyl-2H-indazole-3-carboxamide was thus obtained.

m.p.=167-169° C.
Elemental analysis for C, 21; H, 24; N, 4; O

|  | C | H | N |
|---|---|---|---|
| Found % | 72.21 | 7.02 | 16.09 |
| Calculated % | 72.39 | 6.94 | 16.08 |

$^1$H-NMR (DMSO-d$_6$, δ ppm): 1.66 (dq, J=11.80, 2.90 Hz, 2 H) 1.82-1.94 (m, 2 H) 2.09 (t, J=10.67 Hz, 2 H) 2.83 (d, J=11.69 Hz, 2 H) 3.49 (s, 2 H) 3.76-3.95 (m, 1 H) 4.27 (s, 3 H) 7.19 (ddd, J=8.18, 6.87, 1.02 Hz, 1 H) 7.24-7.38 (m, 6 H) 7.66 (d, J=8.77 Hz, 1 H) 7.72 (d, J=8.48 Hz, 1 H) 8.48 (d, J=7.89 Hz, 1 H).

EXAMPLE 22

N-{1-[3-(4-fluorophenyl)propyl]piperidin-4-yl}-2-methyl-2H-indazole-3-carboxamide (Compound No. 22)

(Compound I: R1=H, R2=CH$_3$, X=—C(O)N(R5)-, R3=4-F, R4=H, R5=H, R6+R7=—CH$_2$—CH$_2$—, n=0, p=2, m=3, Y=CH, W=N)

22a) 1-[3-(4-fluorophenyl)propyl]piperidine-4-amine (Compound XI: R3=4-F, R4=H, R6+R7=—CH$_2$—CH$_2$—, Y=CH, W=N, n=0, p=2, m=3)

The product was prepared using the procedure described in Example 7d) using as reactants N-(phenylmethylene)piperidine-4-amine (Example 14a) (1.9 g; 10 mol) and 1-(3-bromopropyl)-4-fluorobenzene (2.2 g; 10 mmol).

1.8 g of 1-[3-(4-fluorophenyl)propyl]piperidine-4-amine was thus obtained, and was used for the next reaction without further purification.

22b) N-{1-[3-(4-fluorophenyl)propyl]piperidin-4-yl}-2-methyl-2H-indazole-3-carboxamide The compound was obtained according to the procedure described in Example 7e) using as reactants 2-methyl-2H-indazole-3-carbonyl chloride (Example 1b) (1.49 g; 7.6 mmol) and 1-[3-(4-fluorophenyl)propyl]piperidine-4-amine (Example 22a) (1.8 g; 7.6 mmol).

165 mg of N-{1-[3-(4-fluorophenyl)propyl]piperidin-4-yl}-2-methyl-2H-indazole-3-carboxamide was thus obtained.

m.p.=162-165° C.
Elemental analysis for C, 23; H, 27; N, 4; OF

|  | C | H | N |
|---|---|---|---|
| Found % | 69.91 | 6.79 | 14.19 |
| Calculated % | 70.03 | 6.90 | 14.20 |

$^1$H-NMR (DMSO-d$_6$, δ ppm): 1.55-1.79 (m, 4 H) 1.88 (d, 2 H) 2.01 (t, J=10.82 Hz, 2 H) 2.28 (t, J=7.16 Hz, 2 H) 2.58 (t, J=7.60 Hz, 2 H) 2.86 (d, J=11.69 Hz, 2 H) 3.71-3.96 (m, 1 H) 4.27 (s, 3 H) 7.09 (t, J=8.92 Hz, 2 H) 7.15-7.35 (m, 4 H) 7.66 (d, J=8.48 Hz, 1 H) 7.73 (d, J=8.48 Hz, 1 H) 8.47 (d, J=7.60 Hz, 1 H).

EXAMPLE 23

N-({1-[2-(2,4-difluorophenyl)ethyl]piperidin-4-yl}methyl)-2-methyl-2H-indazole-3-carboxamide
(Compound No. 23)

(Compound I: R1=H, R2=CH$_3$, X=—C(O)N(R5)-, R3=4-F, R4=2-F, R5=H, R6 +R7=—CH$_2$CH$_2$—, n=1, p=2, m=2, Y=CH, W=N)

23a) {1-[2-(2,4-difluorophenyl)ethyl]-4-piperidine}methanamine (Compound XI: R3=4-F, R4=2-F, R6+R7=—CH$_2$—CH$_2$—, Y=CH, W=N, n=1, p=2, m=2)

{1-[2-(2,4-difluorophenyl)ethyl]-4-piperidine}methanamine was prepared according to the procedure described in Example 7d) using as reactants N-hexahydro-4-pyridinylmethyl-N-phenylmethylidene amine (2.0 g; 10 mmol), and 1-(2-bromoethyl)-2,4-difluorobenzene (2.2 g; 10 mol).

1.9 g of {1-[2-(2,4-difluorophenyl)ethyl]-4-piperidine}methanamine was obtained, and was used without further purification for the next reaction.

23b) N-({1-[2-(2,4-difluorophenyl)ethyl]piperidin-4-yl}methyl)-2-methyl-2H-indazole-3-carboxamide The compound was obtained according to the procedure described in Example 7e) using as reactants 2-methyl-2H-indazole-3-carbonyl chloride (Example 1b) (1.45 g; 7.4 mmol) and {1-[2-(2,4-difluorophenyl)ethyl]-4-piperidine}methanamine (Example 23a) (1.9 g; 7.4 mmol).

350 mg of N-({1-[2-(2,4-difluorophenyl)ethyl]piperidin-4-yl}methyl)-2-methyl-2H-indazole-3-carboxamide was thus obtained.

m.p.=122-126° C.
Elemental analysis for C, 23; H, 26; N, 4; OF, 2

|  | C | H | N |
| --- | --- | --- | --- |
| Found % | 66.81 | 6.39 | 13.39 |
| Calculated % | 66.97 | 6.35 | 13.58 |

$^1$H-NMR (DMSO-d$_6$, δ ppm): 1.23 (qd, J=11.79, 3.51 Hz, 2 H) 1.48-1.80 (m, 3 H) 1.96 (t, J=10.96 Hz, 2 H) 2.47 (t, J=7.50 Hz, 2 H) 2.74 (t, J=7.45 Hz, 2 H) 2.93 (d, J=11.40 Hz, 2 H) 3.25 (t, J=6.28 Hz, 2 H) 4.29 (s, 3 H) 6.95-7.04 (m, 1 H) 7.09-7.25 (m, 2 H) 7.27-7.42 (m, 2 H) 7.67 (d, J=8.77 Hz, 1 H) 7.77 (d, J=8.18 Hz, 1 H) 8.54 (t, J=5.70 Hz, 1 H).

Pharmacology

Test A

Binding to the rat 5-HT$_{2A}$ serotonin receptor was effected using, as starting material, a preparation of membranes from homogenate of rat cerebral cortex, preincubated for 15 minutes at 37° C. and pretreated with 100 nM prazosin and 100 nM pyrilamine for preventing binding of [3H]-ketanserin to the α$_1$ adrenergic and H1 histaminergic receptors.

Displacement studies were conducted using 1 nM [3H]-ketanserin as radioligand. This concentration was selected on the basis of saturation studies using various concentrations of radioligand (from 0.04 nM to 10 nM) which made it possible to obtain a Bmax of 709.9 nM and a Kd of 1.7 nM.

The non-specific binding was measured in the presence of 10 μM methysergide. The assay was conducted in Tris-HCl 50 mM buffer (pH 7.4 at 37° C.), with incubation for 2 hours at 37° C. The test compounds were dissolved in DMSO, then diluted in buffer (final DMSO concentration 0.01%) and plated on 96-well plates. Methysergide and/or ketanserin were used as reference compounds.

Binding is initiated by addition of 200 μl of homogenate (450 μg/ml protein content); after incubation, the membranes were filtered on glass-fibre filters (GF/B) (Unifilter, Packard) treated with 0.3% polyethyleneimine. Then the filters were washed with buffer solution and stove-dried for 30 minutes at 45° C. The scintillation liquid was added to each well, and 10 hours later the radioactivity was measured for 1 minute using a TopCount (Packard). The test compounds were tested in duplicate at 8 concentrations (from 10-12 to 10-5 M).

The IC50 values for each compound were calculated using non-linear regression analysis (GraphPad PRISM software) and the inhibition constants Ki were determined using the equation described by Cheng Y. and Prussof W. H. (1973) "Relationship between the inhibition constant (Ki) and the concentration of inhibitor which causes 50 percent inhibition (I50) of an enzyme reaction." Biochem. Pharmacol. 22: 3099-3108.

Test B

Binding to the serotonin 5-HT$_{1A}$ receptor was effected using standard methods described in Martin G. R. and Humphrey P. P. A. (1994) "Receptor for 5-hydroxytryptamine: current perspectives on classification and nomenclature." Neuropharmacol. 33: 261-273 and in May J. A., McLaughlin M. A., Sharif N. A., Hellberg M. R. and Dean T. R. (2003) "Evaluation of the ocular hypotensive response of serotonin 5-HT$_{1A}$ and 5-HT$_2$ receptor ligands in conscious ocular hypertensive cynomolgus monkeys." J. Pharmacol. Exp. Ther. 306(1): 301-309. Recombinant CHO cells for expression of the human enzyme and metergoline as reference compound were used as the starting material. The test compounds were tested in duplicate at a single concentration of 1 μM.

Binding to the serotonin 5-HT$_{1B}$ receptor was effected using standard methods described in Hoyer D., Engel G. and Kalkman H. O. (1985) "Characterization of the 5-HT$_{1B}$ recognition site in rat brain: binding studies with (-)[125I]iodocyanopindolol." Eur. J. Pharmacol. 18: 1-12. A homogenate from Wistar rat cerebral cortex was used as starting material, and serotonin as reference compound. The test compounds were tested in duplicate at a single concentration of 1 μM.

Binding to the serotonin 5-HT$_{1D}$ receptor was effected using standard methodology described in: Heuring R. E. and Peroutka S. J. (1987) "Characterization of a novel 3H-5-hydroxytryptamine binding site subtype in bovine brain membranes." J. Neurosci. 7(3): 894-903. A homogenate from bovine cerebral caudatum was used as starting material, and serotonin as reference compound. The test compounds were tested in duplicate at a single concentration of 1 μM.

Binding to the human serotonin 5-HT$_{2A}$ receptor was effected by the standard methodology described in Bonhaus D. W., Bach C., De Souza A., Salazar F. H., Matsuoka B. D., Zuppan P., Chan H. W., Eglen R. M. (1995) "The pharmacology and distribution of human 5-hydroxytryptamine2B (5-HT$_{2B}$) receptor gene products: comparison with 5-HT$_{2A}$ and 5-HT$_{2C}$ receptors." Br. J. Pharmacol. 115(4): 622-628; and Saucier C., Albert P. R. (1997) "Identification of an endogenous 5-hydroxytryptamine2A receptor in NIH-3T3 cells: agonist-induced down-regulation involves decreases in receptor RNA and number." J. Neurochem. 68(5): 1998-2011. The test compounds were tested in duplicate at a single concentration of 1 µM and then at six concentrations to find the pKi values of the individual compounds.

Binding to the serotonin 5-HT$_{2B}$ receptor was effected using the standard methodology described in Bonhaus D. W., Bach C., De-Souza A., Rich Salazar F. H., Matsuoka B. D., Zuppan P., Chan H. W. and Eglen R. M. (1995) "The pharmacology and distribution of human 5-hydroxytryptamine2B (5-HT$_{2B}$) receptor gene products: comparison with 5-HT$_{2A}$ and 5-HT$_{2C}$ receptors." Br. J. Pharmacol. 115: 622-628. CHO-K1 recombinant cells for expression of the human enzyme were used as starting material, and ketanserin as reference compound.: The test compounds were tested in duplicate at a single concentration of 1 µM.

Binding to the serotonin 5-HT$_{2C}$ receptor was effected using the standard methodology described in: Wolf W. A. and Schutz J. S. (1997) "The serotonin 5-HT$_{2C}$ receptor is a prominent serotonin receptor in basal ganglia: evidence from functional studies on serotonin-mediated phosphoinositide hydrolysis." J. Neurochem. 69: 1449-1458. CHO-K1 recombinant cells for expression of the human enzyme were used as starting material, and SB242084 as reference compound. The test compounds were tested in duplicate at a single concentration of 1 µM and then at six concentrations to find the pKi values of the individual compounds.

Binding to the serotonin 5-HT$_3$ receptor was effected using standard methodology described in: Boess F. G., Steward L. J., Steele J. A., Liu D., Reid J., Glencorse T. A. and Martin I. L. (1997) "Analysis of the ligand binding site of the 5-HT$_3$ receptor using site-directed mutagenesis: importance of glutamate 106." Neuropharmacology 36: 637-647 and in Millerk W. E., Fletcher P. W. and Teitler M. (1992) "Membrane-bound and solubilized brain 5-HT$_3$ receptor: improved radioligand binding assay using bovine area postrema or rat cortex and the radioligand [3H]GR65630, [3H]BRL43694, and [3H]LY278584." Synapse 11: 58-66. HEK293 recombinant cells for expression of the human enzyme were used as starting material, and MDL-72222 as reference compound. The test compounds were tested in duplicate at a single concentration of 1 µM.

Binding to the serotonin 5-HT$_4$ receptor was effected using standard methodology described in: Grossman C. J., Kilpatrick G. J. and Bunce K. T. (1993) "Development of a radioligand binding assay for 5-HT$_4$ receptors in guinea-pig and rat brain." Br. J. Pharmacol. 109: 618-624. A homogenate from guinea-pig cerebral striatum was used as starting material, and RS-23597190 as reference compound. The test compounds were tested in duplicate at a single concentration of 1 µM.

The selectivity of the test compounds for the 5-HT$_{4(b)}$ receptor of human recombinant cells was determined using a procedure derived from the standard methodology described in Mialet J., Berque-Bestel I., Eftekhari P., Gastineau M., Giner M., Dahmoune Y., Donzeau-Gouge P., Hoebeke J., Langlois M., Sicsic S., Fischmeister R. and Lezoualc'h F. (2000) "Isolation of the serotoninergic 5-HT4(e) receptor from human heart and comparative analysis of its pharmacological profile in C6-glial and CHO cell lines." Br. J. Pharmacol. 129: 771-781.

Binding to the 5-HT$_{4(b)}$ receptor was effected using a preparation of HEK293 recombinant cells for human 5-HT$_4$(b) receptor as starting material. On the day of the experiment, a cellular pellet stored at −80° C. was thawed and kept in ice. The pellet was then homogenized in buffer (25 mM Tris-HCl pH 7.4; 0.1 mM EDTA) and the suspension was centrifuged at 30000 g for 20 minutes. The pellet was washed three times in washing buffer and finally resuspended in incubation buffer (25 mM Tris-HCl pH 7.4; 0.5 mM EDTA; 10 mM MgSO$_4$) at a final concentration of approx. 6×10$^5$ cells/ml. Displacement studies were conducted using 0.2 nM [3H]-GR113808 as radioligand. This concentration was selected on the basis of studies of saturation using various concentrations of radioligand (from 0.02 nM to 2.5 nM). Non-specific binding was measured in the presence of 10 µM Piboserod. The assay was carried out in a total volume of 250 µl of buffer 25 mM Tris-HCl pH 7.4; 0.5 mM EDTA; 10 mM MgSO$_4$ with incubation for 2 hours at 27° C. The test compounds were dissolved in DMSO and then diluted in buffer (final concentration of DMSO equal to 0.01%) and plated. on 96-well plates. Piboserod was used as reference compound. Binding was initiated by addition of 200 µl of cellular homogenate (35-92 µg/ml protein content); after incubation, the membranes were filtered on glass-fibre filters (GF/B) (Unifilter, Packard) treated with 0.1% polyethylimine. Then the filters were washed with buffer and stove-dried for 30 minutes at 45° C. The scintillation liquid was added to each well, and 16 hours later the radioactivity was measured for 1 minute using a TopCount (Packard). The protein concentration was determined using the BCA method (Pierce) with BSA as standard. The test compounds were tested in duplicate at 8 concentrations (from 10-12 to 10-5 M), the IC50 values were calculated for each compound using non-linear regression analysis (GraphPad PRISM software) and the inhibition constants Ki were determined using the equation described by Cheng Y. and Prussof W. H. (1973) "Relationship between the inhibition constant (Ki) and the concentration of inhibitor which causes 50 percent inhibition (I50) of an enzyme reaction." Biochem. Pharmacol. 22: 3099-3108.

Binding to the serotonin 5-HT$_{5(A)}$ receptor was effected using the standard methodology described in Rees S., den Daas I., Foord S., Goodson S., Bull D., Kilpatriele G. and Lee M. (1994) "Cloning and characterization of the human 5-HT$_{5A}$ serotonin receptor." FEBS Lett. 355: 242-246. CHO-K1 recombinant cells for expression of the human enzyme were used as starting material, and methiothepin as reference compound. The test compounds were tested in duplicate at a single concentration of 1 µM.

Binding to the serotonin 5-HT$_6$ receptor was effected using the standard methodology described in Monsma F. J. Jr, Shen Y., Ward R. P., Hamblin M. W. and Sibley D. R. (1993) "Cloning and expression of a novel serotonin receptor with high affinity for tricyclic psychotropic drugs." Mol. Pharmacol. 43: 320-327. HeLa recombinant cells for expression of the human receptor were used as starting material, and methiothepin as reference compound. The test compounds were tested in duplicate at a single concentration of 1 µM.

Binding to the serotonin 5-HT$_7$ receptor was effected using the standard methodology described in Roth B. L, Craigo S. C., Choudhary M. S., Uluer S., Monsma F. J. Jr, Shen Y., Meltzer H. Y. and Sibley D. R. (1994) "Binding of typical and atypical antipsychotic agents to 5-hydroxytryptamine-6 and 5-hydroxytryptamine-7 receptors." J. Pharmacol. Exp. Ther. 268: 1403-1410 and in Shen Y., Monsma F. J. Jr, Metcalf M. A., Jose P. A., Hamblin M. W. and Sibley D. R. (1993) "Molecular cloning and expression of a 5-hydroxytryptamine 7 serotonin receptor subtype." J. Biol. Chem. 268: 18200-18204. CHO recombinant cells for expression of the human receptor were used as starting material, and methiothepin as reference compound. The test compounds were tested in duplicate at a single concentration of 1 µM.

Binding to the serotonin transporter was effected using the standard methodology described in Shearman L. P., McReynolds A. M., Zhou F. C., Meyer J. S. (1998) "Relationship between [125I]RTI-55-labeled cocaine binding sites and the serotonin transporter in rat placenta." Am. J. Physiol. 275(6 Pt 1): C1621-1629 and in Wolf W. A. and Kuhn D. M. (1992) "Role of essential sulfhydryl groups in drug interactions at the neuronal 5-HT transporter. Differences between amphetamines and 5-HT uptake inhibitors." J. Biol. Chem. 267(29): 20820-20825. HEK293 recombinant cells for expression of the human transport system were used as starting material, and fluoxetine as reference compound. The test compounds were tested in duplicate at a single concentration of 1 µM.

The cellular assay of serotonin incorporation was effected using standard methodology described in Gu H., Wall S. and Rudnick G. (1994) "Stable expression of biogenic amine transporter reveals differences in inhibitor sensitivity, kinetics, and ion dependence." J. Biol. Chem. 269(10): 7124-7130. HEK293 cells were used, and fluoxetine as reference compound. The test compounds were tested in duplicate at a single concentration of 10 µM.

Test C

Male CD-1 mice weighing 25-30 g were used for the head twitch test in the mouse. The animals were treated intraperitoneally with the test compounds (5 mg/kg) suspended in methylcellulose (MTC). The control animals were treated with just the vehicle (MTC) by the same route.

Half an hour after treatment with the test compounds, the animals were given an intraperitoneal injection of 5-hydroxytryptophan (5-HTP; 300 mg/kg), serotonin precursor, for the purpose of inducing "head twitches", a characteristic shaking of the head induced in the animals by the increase in central levels of serotonin.

The number of head twitches, which constitutes the parameter for assessment of the serotoninergic response, was measured in the interval from 24 to 26 minutes after administration of 5-HTP.

As shown in FIG. 1, the compounds of the invention induce a reduction in the number of head twitches compared with the animals treated with MTC alone, demonstrating the capacity for antagonizing the serotoninergic effects induced by administration of 5-HTP.

The invention claimed is:

1. A compound which is selected from the group consisting of

N,2-dimethyl-N-{[1-(2-phenylethyl)piperidin-4-yl]methyl}-2H-indazole-3-carboxamide hydrochloride hemihydrate;

N-({1-[2-(4-hydroxyphenyl)ethyl]piperidin-4-yl}methyl)-5-methoxy-2-methyl-2H-indazole-3-carboxamide;

N-({1[2-(4-fluorophenyl)ethyl]piperidin-4-yl}methyl)-2-(2-methoxyethyl)-2-H-indazole-3-carboxamide hydrochloride;

N-({1-[2-(4-fluorophenyl)ethyl]piperidin-4-yl}methyl)-2-methyl-2H-indazole-3-carboxamide hydrochloride;

2-(2,4-difluorophenyl)-N-({1-[(2-methyl-2H-indazole-3-yl)carbonyl]piperidin-4-yl}methyl)ethanamine hydrochloride; and 2-(4-fluorophenyl)-N-({1-[(2-methyl-2H-indazol-3-yl)carbonyl)piperidin-4-yl}methyl]ethanamine hydrochloride, or a pharmaceutically acceptable salt of said compound.

2. The compound or pharmaceutically acceptable salt thereof according to claim 1 which is N,2-dimethyl-N-{[1-(2-phenylethyl)piperidin-4-ylimethyl}-2H-indazole-3-carboxamide hydrochloride hemihydrate or a pharmaceutically acceptable salt thereof.

3. The compound or pharmaceutically acceptable salt thereof according to claim 1 which is N-({1-[2-(4-hydroxyphenyl)ethyl]piperidin-4-yl}methyl)-5-methoxy-2-methyl-2H-indazole-3-carboxamide or a pharmaceutically acceptable salt thereof.

4. The compound or pharmaceutically acceptable salt thereof according to claim 1 which is N-({1-[2-(4-fluorophenyl)ethyl]piperidin-4-yl}methyl)-2-(2-methoxyethyl)-2-H-indazole-3-carboxamide hydrochloride or a pharmaceutically acceptable salt thereof.

5. The compound or pharmaceutically acceptable salt thereof according to claim 1 which is N-({1-[2-(4-fluorophenyl)ethyl]piperidin-4-yl}methyl)-2-methyl-2H-indazole-3-carboxamide hydrochloride or a pharmaceutically acceptable salt thereof.

6. The compound or pharmaceutically acceptable salt thereof according to claim 1 which is 2-(2,4-difluorophenyl)-N-({1-[(2-methyl-2H-indazole-3-yl)carbonyl]piperidin-4-yl}methyl)ethanamine hydrochloride or a pharmaceutically acceptable salt thereof.

7. The compound or pharmaceutically acceptable salt thereof according to claim 1 which is 2-(4-fluorophenyl)-N-({1-[(2-methyl-2H-indazol-3-yl)carbonyl)piperidin-4-yl}methyl]ethanamine hydrochloride or a pharmaceutically acceptable salt thereof.

8. A pharmaceutical composition, comprising at least one 2-alkyl-indazole compound or salt according to claim 1 and at least one pharmaceutically acceptable excipient.

* * * * *

UNITED STATES PATENT AND TRADEMARK OFFICE
CERTIFICATE OF CORRECTION

PATENT NO. : 8,507,528 B2
APPLICATION NO. : 12/516091
DATED : August 13, 2013
INVENTOR(S) : Maria Alessandra Alisi et al.

It is certified that error appears in the above-identified patent and that said Letters Patent is hereby corrected as shown below:

On the title page, Item (30), the Foreign Application Priority Data is incorrect. Item (30) should read:

--(30) Foreign Application Priority Data

Nov. 22, 2006 (IT)................................ MI2006 A 002230--

Signed and Sealed this
Eighth Day of October, 2013

Teresa Stanek Rea
*Deputy Director of the United States Patent and Trademark Office*